US012558022B2

(12) United States Patent
Thigpen et al.

(10) Patent No.: US 12,558,022 B2
(45) Date of Patent: Feb. 24, 2026

(54) MENSTRUAL CYCLE TRACKING

(71) Applicant: Oura Health Oy, Oulu (FI)

(72) Inventors: Nina Nicole Thigpen, Jersey City, NJ
(US); Neta A. Gotlieb, Albany, CA
(US); Gerald Pho, Sommerville, MA
(US); Kirstin Elizabeth Aschbacher,
San Francisco, CA (US)

(73) Assignee: Oura Health Oy, Oulu (FI)

( * ) Notice: Subject to any disclaimer, the term of this
patent is extended or adjusted under 35
U.S.C. 154(b) by 790 days.

(21) Appl. No.: 17/692,407

(22) Filed: Mar. 11, 2022

(65) Prior Publication Data

US 2022/0287622 A1     Sep. 15, 2022

Related U.S. Application Data

(60) Provisional application No. 63/160,315, filed on Mar.
12, 2021.

(51) Int. Cl.
A61B 5/00       (2006.01)
A61B 5/01       (2006.01)
A61B 5/024      (2006.01)
A61B 5/08       (2006.01)

(52) U.S. Cl.
CPC ............. A61B 5/4325 (2013.01); A61B 5/01
(2013.01); A61B 5/024 (2013.01); A61B
5/0816 (2013.01); A61B 5/7275 (2013.01);
A61B 5/7282 (2013.01); A61B 5/742
(2013.01)

(58) Field of Classification Search
CPC ......... A61B 5/01; A61B 5/024; A61B 5/0816;
A61B 5/4325; A61B 5/7239; A61B 5/7275; A61B 5/7282; A61B 5/742; A61B
10/0012; A61B 2010/0019
See application file for complete search history.

(56) References Cited

U.S. PATENT DOCUMENTS

| | | | |
|---|---|---|---|
| 8,496,597 | B2 | 7/2013 | James et al. |
| 9,155,522 | B2 | 10/2015 | James et al. |
| 9,155,523 | B2 | 10/2015 | James et al. |
| 2018/0035954 | A1 | 2/2018 | Swezey |
| 2018/0042540 | A1* | 2/2018 | Kinnunen .......... A61B 5/02433 |

(Continued)

FOREIGN PATENT DOCUMENTS

EP          2061380 B2     3/2019

OTHER PUBLICATIONS

International Search Report and Written Opinion—PCT/US2022/
019972—ISA/EPO—Jun. 27, 2022.

*Primary Examiner* — Eric F Winakur
*Assistant Examiner* — Sienna C Pyle
(74) *Attorney, Agent, or Firm* — Holland & Hart LLP

(57) ABSTRACT

Methods, systems, and devices for menstrual cycle phase
identifier are described. A system may be configured to
receive physiological data collected over a plurality of days,
where the physiological data includes at least temperature
data. Additionally, the system may be configured to deter-
mine a time series of temperature values taken over the
plurality of days where the time series includes a plurality of
menstrual cycles for the user. The system may then identify
morphological features in the time series and identify men-
strual cycle phases in the time series based on the morpho-
logical features. The system may cause the graphical user
interface to display the identified menstrual cycle phases.

24 Claims, 13 Drawing Sheets

(56)            References Cited

U.S. PATENT DOCUMENTS

| | | |
|---|---|---|
| 2019/0110692 A1 | 4/2019 | Pardey et al. |
| 2019/0167237 A1 | 6/2019 | Stein et al. |
| 2020/0000441 A1* | 1/2020 | Lafon ................ A61B 5/02438 |
| 2022/0047250 A1* | 2/2022 | Clements ............... G01K 1/024 |
| 2022/0233102 A1* | 7/2022 | Shelton, IV ........... G16H 40/60 |

* cited by examiner

Sleep Period

510

505

500-a

Portion of Sleep Period
(First 110–210 min)

520

515

500-b

Portion of Sleep Period
(Last 110–210 min)

530

525

500-c

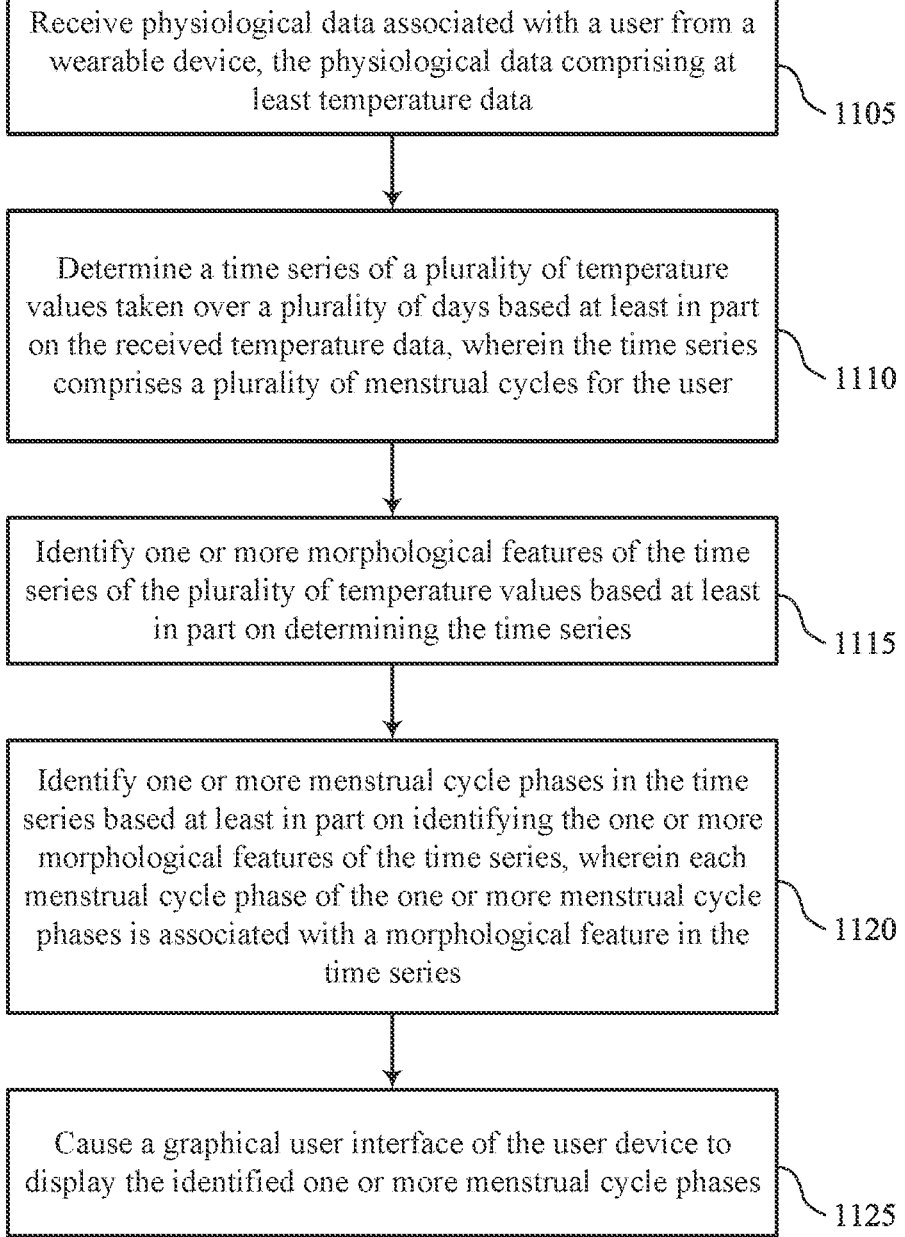

Receive physiological data associated with a user from a wearable device, the physiological data comprising at least temperature data

1105

Determine a time series of a plurality of temperature values taken over a plurality of days based at least in part on the received temperature data, wherein the time series comprises a plurality of menstrual cycles for the user

1110

Identify one or more morphological features of the time series of the plurality of temperature values based at least in part on determining the time series

1115

Identify one or more menstrual cycle phases in the time series based at least in part on identifying the one or more morphological features of the time series, wherein each menstrual cycle phase of the one or more menstrual cycle phases is associated with a morphological feature in the time series

1120

Cause a graphical user interface of the user device to display the identified one or more menstrual cycle phases

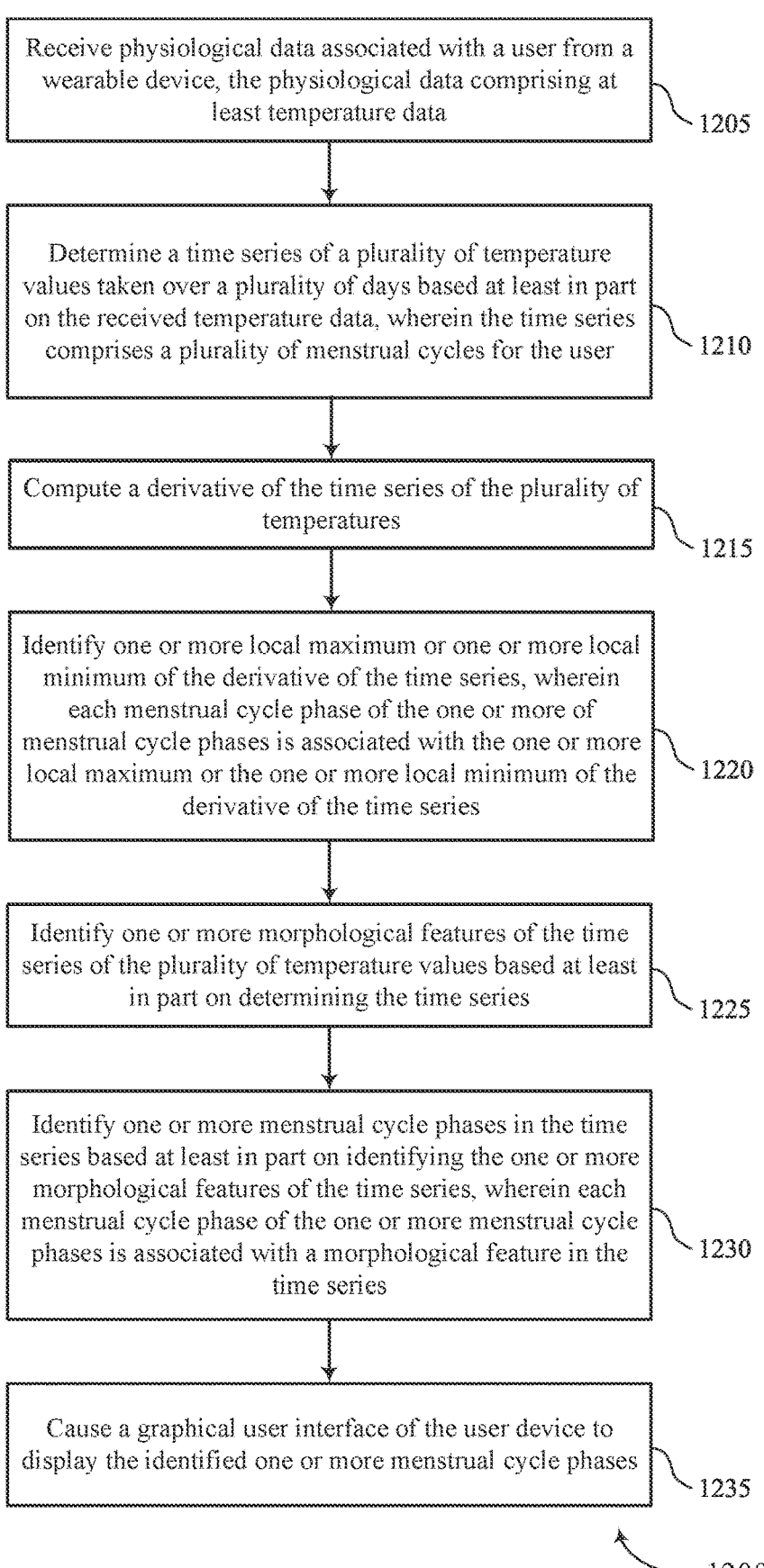

Receive physiological data associated with a user from a wearable device, the physiological data comprising at least temperature data ⟍ 1205

Determine a time series of a plurality of temperature values taken over a plurality of days based at least in part on the received temperature data, wherein the time series comprises a plurality of menstrual cycles for the user ⟍ 1210

Compute a derivative of the time series of the plurality of temperatures ⟍ 1215

Identify one or more local maximum or one or more local minimum of the derivative of the time series, wherein each menstrual cycle phase of the one or more of menstrual cycle phases is associated with the one or more local maximum or the one or more local minimum of the derivative of the time series ⟍ 1220

Identify one or more morphological features of the time series of the plurality of temperature values based at least in part on determining the time series ⟍ 1225

Identify one or more menstrual cycle phases in the time series based at least in part on identifying the one or more morphological features of the time series, wherein each menstrual cycle phase of the one or more menstrual cycle phases is associated with a morphological feature in the time series ⟍ 1230

Cause a graphical user interface of the user device to display the identified one or more menstrual cycle phases ⟍ 1235

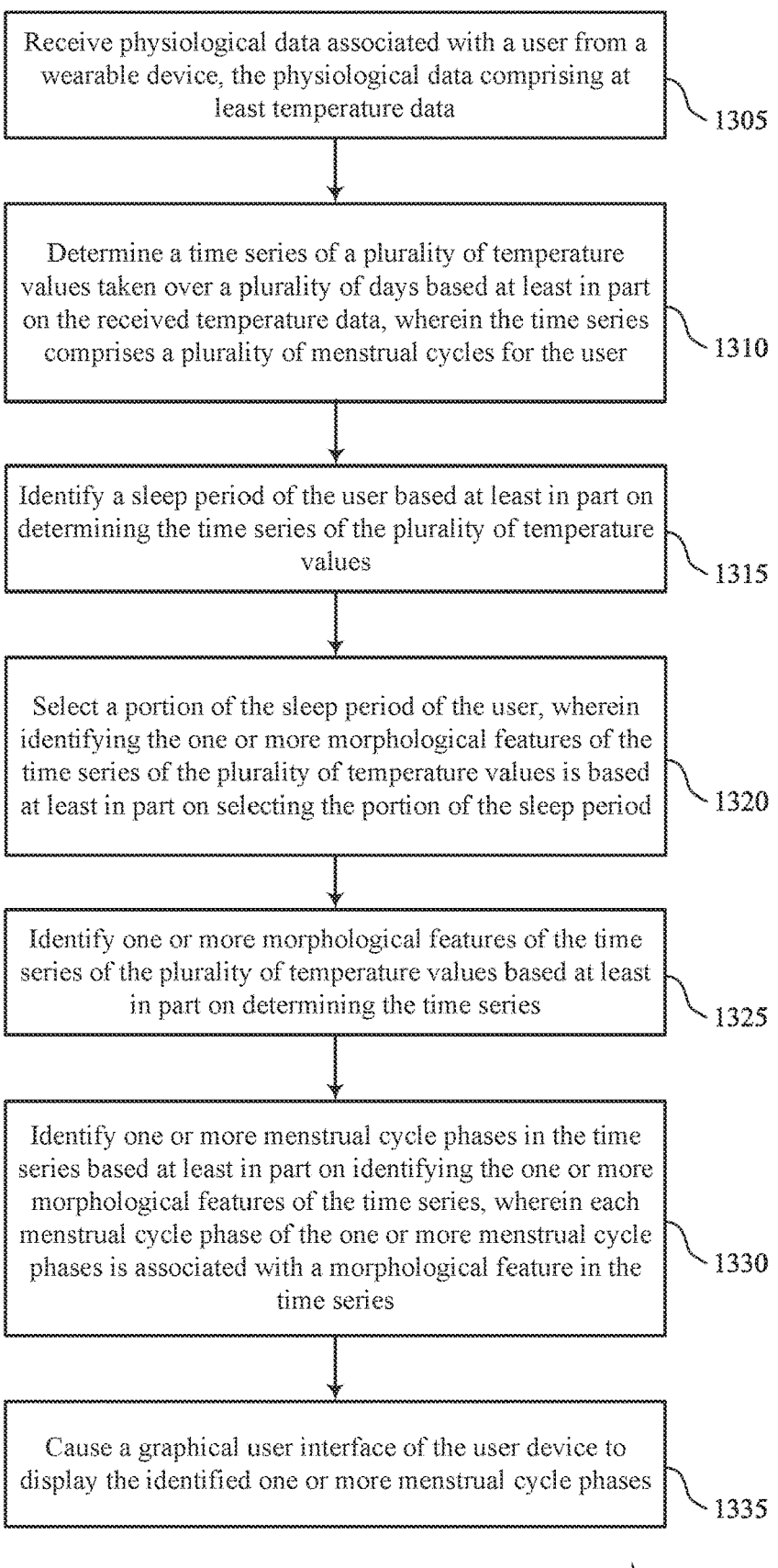

Receive physiological data associated with a user from a wearable device, the physiological data comprising at least temperature data
1305

Determine a time series of a plurality of temperature values taken over a plurality of days based at least in part on the received temperature data, wherein the time series comprises a plurality of menstrual cycles for the user
1310

Identify a sleep period of the user based at least in part on determining the time series of the plurality of temperature values
1315

Select a portion of the sleep period of the user, wherein identifying the one or more morphological features of the time series of the plurality of temperature values is based at least in part on selecting the portion of the sleep period
1320

Identify one or more morphological features of the time series of the plurality of temperature values based at least in part on determining the time series
1325

Identify one or more menstrual cycle phases in the time series based at least in part on identifying the one or more morphological features of the time series, wherein each menstrual cycle phase of the one or more menstrual cycle phases is associated with a morphological feature in the time series
1330

Cause a graphical user interface of the user device to display the identified one or more menstrual cycle phases
1335

FIG. 13                                                    1300

MENSTRUAL CYCLE TRACKING

CROSS REFERENCE

The present Application for Patent claims the benefit of U.S. Provisional Patent Application No. 63/160,315 by Aschbacher et al., entitled "MENSTRUAL AND OVARIAN CYCLE TRACKING," filed Mar. 12, 2021, assigned to the assignee hereof, and expressly incorporated by reference herein.

FIELD OF TECHNOLOGY

The following relates to wearable devices and data processing, including menstrual cycle tracking.

BACKGROUND

Some wearable devices may be configured to collect data from users associated with body temperature and heart rate. For example, some wearable devices may be configured to detect cycles associated with women's health. However, conventional cycle detection techniques implemented by wearable devices are deficient.

BRIEF DESCRIPTION OF THE DRAWINGS

FIGS. 11 through 13 show flowcharts illustrating methods that support menstrual cycle tracking in accordance with aspects of the present disclosure.

DETAILED DESCRIPTION

Figure 1:
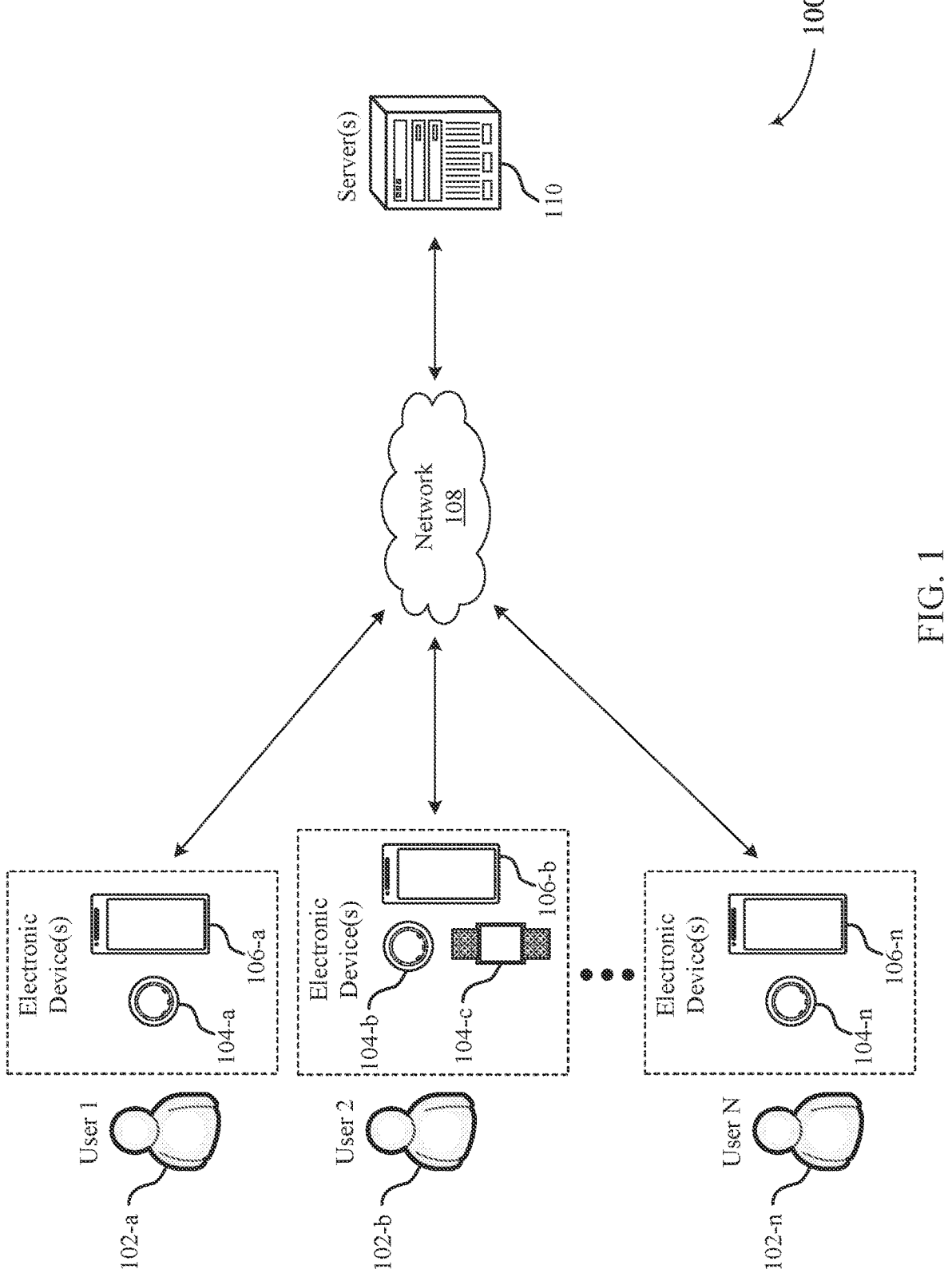
FIG. 1 illustrates an example of a system that supports menstrual cycle tracking in accordance with aspects of the present disclosure.

Some wearable devices may be configured to collect physiological data from users, including temperature data, heart rate data, and the like. Acquired physiological data may be used to analyze the user's movement and other activities, such as sleeping patterns. Many users have a desire for more insight regarding their physical health, including their sleeping patterns, activity, and overall physical well-being. In particular, many users may have a desire for more insight regarding women's health, including their menstrual cycle, ovulation, and fertility patterns. However, typical cycle tracking or women's health devices and applications lack the ability to provide robust prediction and insight for several reasons.

First, typical cycle prediction applications require users to manually take their temperature with a device at a discrete time each day. This single temperature data point may not provide sufficient context to accurately capture or predict the true temperature variations indicative of woman's health cycle patterns, and may be difficult to accurately capture given the sensitivity of the measuring device to user movement or exertion. Second, even for devices that are wearable or that take a user's temperature more frequently throughout the day, typical devices and applications lack the ability to collect other physiological, behavioral, or contextual inputs from the user that can be combined with the measured temperature to more comprehensively understand the complete set of physiological contributors to a women's cycle.

Aspects of the present disclosure are directed to techniques for menstrual cycle tracking. In particular, computing devices of the present disclosure may receive physiological data including temperature data, among other forms of physiological data, from the wearable device associated with the user and determine a time series of temperature values taken over a plurality of days. For example, aspects of the present disclosure may identify one or more morphological features from a graphical representation of a time series of collected physiological data, such as negative slopes, positive slopes, maximum temperatures, minimum temperatures, patterns, axis crossings, or a combination thereof of the time series of the physiological data. As such, aspects of the present disclosure identify one or more menstrual cycle phases in the time series based on identifying the morphological features. The menstrual cycle phase may be representative of menstruation, an ovarian cycle, a uterine cycle, a sub-phase of any one of the menstruation, the ovarian cycle, the uterine cycle, or a combination thereof. In some cases, the menstrual cycle phase may representative of a reproductive cycle and/or a sub-phase of the reproductive cycle.

Each menstrual cycle phase of the one or more menstrual cycle phases may be associated with a morphological feature in the time series and/or one or more additional morphological features in the time series of temperature values. In some implementations, the system may analyze historical temperature data from a user and identify a plurality of menstrual cycle phases for a plurality of previous menstrual cycles and may generate an indication to a user that indicates the user's previous menstrual cycles. The user may confirm whether the menstrual cycle phases actually occurred on the dates indicated by the system for the historical data, and the system may incorporate this user input into a predictive function (e.g., a machine learning model for predicting future menstrual cycle phases). The system may also analyze temperature series data in real time and may predict an upcoming menstrual cycle phase (e.g., a first day of a menstrual cycle) based on identifying one or more morphological features in the time series of the temperature data and/or based on the user's input from the previous menstrual cycles.

For the purposes of the present disclosure, the term "menstrual cycle" may be used to refer to a user's cycle including a series of natural changes in hormone production and the structures of the uterus and ovaries of the female reproductive system that make pregnancy possible. A menstrual cycle begins with the first day of the user's period, or menstruation, and starts over again when the next period begins. Menstruation is a woman's monthly bleeding, often called a period. For example, a user may be experiencing a first day of a menstrual cycle when the user's body discards the monthly buildup of the lining of the uterus. The menstrual cycle may include menstruation, an ovarian cycle, a uterine cycle, a follicular phase, a luteal phase, or a combination thereof.

Some aspects of the present disclosure are directed to the detection of the menstrual cycle onset before the user experiences symptoms and effects of the menstrual cycle onset. However, techniques described herein may also be used to detect the menstrual cycle onset in cases where the user does not become symptomatic, or does not become aware of their symptoms. In some implementations, the computing devices may identify menstrual cycle phases using a temperature sensor. In such cases, the computing devices may estimate the retrospective dates of period onset and ovulation without the user tagging or labeling these events.

In conventional systems, the user may tag or label events associated with the menstrual cycle and calculate the future menstruation onset day based on an average length between menstrual cycles (e.g., referred to as the calendar method). In other systems, the retrospective events (e.g., period and ovulation) may be estimated using basal body temperature measured once daily (e.g., in the morning) with an oral thermometer. Techniques described herein may continuously collect the physiological data from the user based on measurements taken from a wearable that continuously measures a user's surface temperature and signals extracted from blood flow such as arterial blood flow. In some implementations, the computing devices may sample the user's temperature continuously throughout the day and night. Sampling at a sufficient rate (e.g., one sample per minute) throughout the night (or at certain phases of the night and/or during certain phases of a sleep cycle, as described in more detail below) may provide sufficient temperature data for analysis described herein.

In some cases, continuous temperature measurement at the finger may capture temperature fluctuations (e.g., small or large fluctuations) that may not be evident in core temperature. For example, continuous temperature measurement at the finger may capture minute-to-minute or hour-to-hour temperature fluctuations that provide additional insight that may not be provided by other temperature measurements elsewhere in the body or if the user were manually taking their temperature once per day. As such, data collected by the computing devices may be used to identify when the user experiences a first day of a menstrual cycle.

Techniques described herein may notify a user of the identified menstrual cycle phase in a variety of ways. For example, a system may cause a graphical user interface (GUI) of a user device to display a message or other notification to notify the user of the identified menstrual cycle phase, notify the user of an estimated future menstrual cycle phase, and make recommendations to the user. In one example, the GUI may display a time interval during which the future menstrual cycle phase is predicted to occur and recommendations that the user prepare for a first day of a menstrual cycle based on previously input symptoms. In some implementations, the system may make tag recommendations to users. For example, the system may recommend period, mood, and symptom tags (e.g., cramps, headache) to users at determined times in their cycle (e.g., in a personalized manner). The system may recommend the tags based on their prior history of temperature data, personalized cycling patterns, and/or their prior symptom history.

The system may also include graphics/text which indicates the data used to make the detection/prediction of an upcoming menstrual cycle phase. For example, the GUI may display a notification that an upcoming menstrual cycle phase has been predicted based on temperature deviations from a normal baseline. In some cases, the GUI may display a notification that an upcoming menstrual cycle phase has been predicted based on heart rate deviations from a normal baseline, breath rate deviations from a normal baseline, or both. Based on the early warnings (e.g., before the user experiences symptoms), a user may take early steps that may help reduce the severity of upcoming symptoms associated with the menstrual cycle phase. Additionally, a user may modify/schedule their daily activities (e.g., work and leisure time) based on the early warnings and estimated future menstrual cycle phase (e.g., an onset of menstruation).

In some implementations, the system may provide symptom correlations that provide users with personalized insights into the relationships between a user's symptoms and the user's menstrual cycle. In some implementations, the system may provide behavioral modification suggestions. For example, the system may provide users with personalized suggestions for types of health behaviors that may help modify their cycle length, regularity, and/or reduce cycle-associated symptoms. In one example, behaviors like high-intensity-interval training (HIIT), resistance training, fasting/caloric restriction, a low glycemic load diet, a ketotic carbohydrate diet, time-restricted feeding, biofeedback to enhance heart rate variability (HRV) prior to bedtime, melatonin ingestion, and cannabidiol (CBD) may provide behavioral means to modify cycle parameters and improve associated symptoms.

Aspects of the disclosure are initially described in the context of systems supporting physiological data collection from users via wearable devices. Additional aspects of the disclosure are described in the context of example timing diagrams and example GUIs. Aspects of the disclosure are further illustrated by and described with reference to apparatus diagrams, system diagrams, and flowcharts that relate to menstrual cycle tracking.

FIG. 1 illustrates an example of a system 100 that supports menstrual cycle tracking in accordance with aspects of the present disclosure. The system 100 includes a plurality of electronic devices (e.g., wearable devices 104, user devices 106) which may be worn and/or operated by one or more users 102. The system 100 further includes a network 108 and one or more servers 110.

The electronic devices may include any electronic devices known in the art, including wearable devices 104 (e.g., ring wearable devices, watch wearable devices, etc.), user devices 106 (e.g., smartphones, laptops, tablets). The electronic devices associated with the respective users 102 may include one or more of the following functionalities: 1) measuring physiological data, 2) storing the measured data, 3) processing the data, 4) providing outputs (e.g., via GUIs) to a user 102 based on the processed data, and 5) communicating data with one another and/or other computing devices. Different electronic devices may perform one or more of the functionalities.

Example wearable devices 104 may include wearable computing devices, such as a ring computing device (hereinafter "ring") configured to be worn on a user's 102 finger, a wrist computing device (e.g., a smart watch, fitness band, or bracelet) configured to be worn on a user's 102 wrist, and/or a head mounted computing device (e.g., glasses/goggles). Wearable devices 104 may also include bands, straps (e.g., flexible or inflexible bands or straps), stick-on sensors, and the like, which may be positioned in other locations, such as bands around the head (e.g., a forehead headband), arm (e.g., a forearm band and/or bicep band), and/or leg (e.g., a thigh or calf band), behind the ear, under the armpit, and the like. Wearable devices 104 may also be attached to, or included in, articles of clothing. For example, wearable devices 104 may be included in pockets and/or pouches on clothing. As another example, wearable device 104 may be clipped and/or pinned to clothing, or may otherwise be maintained within the vicinity of the user 102. Example articles of clothing may include, but are not limited to, hats, shirts, gloves, pants, socks, outerwear (e.g., jackets), and undergarments. In some implementations, wearable devices 104 may be included with other types of devices such as training/sporting devices that are used during physical activity. For example, wearable devices 104 may be attached to, or included in, a bicycle, skis, a tennis racket, a golf club, and/or training weights.

Much of the present disclosure may be described in the context of a ring wearable device 104. Accordingly, the terms "ring 104," "wearable device 104," and like terms, may be used interchangeably, unless noted otherwise herein. However, the use of the term "ring 104" is not to be regarded as limiting, as it is contemplated herein that aspects of the present disclosure may be performed using other wearable devices (e.g., watch wearable devices, necklace wearable device, bracelet wearable devices, earring wearable devices, anklet wearable devices, and the like).

In some aspects, user devices 106 may include handheld mobile computing devices, such as smartphones and tablet computing devices. User devices 106 may also include personal computers, such as laptop and desktop computing devices. Other example user devices 106 may include server computing devices that may communicate with other electronic devices (e.g., via the Internet). In some implementations, computing devices may include medical devices, such as external wearable computing devices (e.g., Holter monitors). Medical devices may also include implantable medical devices, such as pacemakers and cardioverter defibrillators. Other example user devices 106 may include home computing devices, such as internet of things (IoT) devices (e.g., IoT devices), smart televisions, smart speakers, smart displays (e.g., video call displays), hubs (e.g., wireless communication hubs), security systems, smart appliances (e.g., thermostats and refrigerators), and fitness equipment.

Some electronic devices (e.g., wearable devices 104, user devices 106) may measure physiological parameters of respective users 102, such as photoplethysmography waveforms, continuous skin temperature, a pulse waveform, respiration rate, heart rate, heart rate variability (HRV), actigraphy, galvanic skin response, pulse oximetry, and/or other physiological parameters. Some electronic devices that measure physiological parameters may also perform some/all of the calculations described herein. Some electronic devices may not measure physiological parameters, but may perform some/all of the calculations described herein. For example, a ring (e.g., wearable device 104), mobile device application, or a server computing device may process received physiological data that was measured by other devices.

In some implementations, a user 102 may operate, or may be associated with, multiple electronic devices, some of which may measure physiological parameters and some of which may process the measured physiological parameters. In some implementations, a user 102 may have a ring (e.g., wearable device 104) that measures physiological parameters. The user 102 may also have, or be associated with, a user device 106 (e.g., mobile device, smartphone), where the wearable device 104 and the user device 106 are communicatively coupled to one another. In some cases, the user device 106 may receive data from the wearable device 104 and perform some/all of the calculations described herein. In some implementations, the user device 106 may also measure physiological parameters described herein, such as motion/activity parameters.

For example, as illustrated in FIG. 1, a first user 102-a (User 1) may operate, or may be associated with, a wearable device 104-a (e.g., ring 104-a) and a user device 106-a that may operate as described herein. In this example, the user device 106-a associated with user 102-a may process/store physiological parameters measured by the ring 104-a. Comparatively, a second user 102-b (User 2) may be associated with a ring 104-b, a watch wearable device 104-c (e.g., watch 104-c), and a user device 106-b, where the user device 106-b associated with user 102-b may process/store physiological parameters measured by the ring 104-b and/or the watch 104-c. Moreover, an nth user 102-n (User N) may be associated with an arrangement of electronic devices described herein (e.g., ring 104-n, user device 106-n). In some aspects, wearable devices 104 (e.g., rings 104, watches 104) and other electronic devices may be communicatively coupled to the user devices 106 of the respective users 102 via Bluetooth, Wi-Fi, and other wireless protocols.

In some implementations, the rings 104 (e.g., wearable devices 104) of the system 100 may be configured to collect physiological data from the respective users 102 based on arterial blood flow within the user's finger. In particular, a ring 104 may utilize one or more LEDs (e.g., red LEDs, green LEDs) which emit light on the palm-side of a user's finger to collect physiological data based on arterial blood flow within the user's finger. In some implementations, the ring 104 may acquire the physiological data using a combination of both green and red LEDs. The physiological data may include any physiological data known in the art including, but not limited to, temperature data, accelerometer data (e.g., movement/motion data), heart rate data, HRV data, blood oxygen level data, or any combination thereof.

The use of both green and red LEDs may provide several advantages over other solutions, as red and green LEDs have been found to have their own distinct advantages when acquiring physiological data under different conditions (e.g., light/dark, active/inactive) and via different parts of the body, and the like. For example, green LEDs have been found to exhibit better performance during exercise. Moreover, using multiple LEDs (e.g., green and red LEDs) distributed around the ring 104 has been found to exhibit superior performance as compared to wearable devices which utilize LEDs which are positioned close to one another, such as within a watch wearable device. Furthermore, the blood vessels in the finger (e.g., arteries, capillaries) are more accessible via LEDs as compared to blood vessels in the wrist. In particular, arteries in the wrist are positioned on the bottom of the wrist (e.g., palm-side of the wrist), meaning only capillaries are accessible on the top of the wrist (e.g., back of hand side of the wrist), where wearable watch devices and similar devices are typically worn. As such, utilizing LEDs and other sensors within a ring 104 has been found to exhibit superior performance as compared to wearable devices worn on the wrist, as the ring 104 may have greater access to arteries (as compared to capillaries), thereby resulting in stronger signals and more valuable physiological data.

The electronic devices of the system 100 (e.g., user devices 106, wearable devices 104) may be communicatively coupled to one or more servers 110 via wired or wireless communication protocols. For example, as shown in FIG. 1, the electronic devices (e.g., user devices 106) may be communicatively coupled to one or more servers 110 via a network 108. The network 108 may implement transfer control protocol and internet protocol (TCP/IP), such as the Internet, or may implement other network 108 protocols. Network connections between the network 108 and the respective electronic devices may facilitate transport of data via email, web, text messages, mail, or any other appropriate form of interaction within a computer network 108. For example, in some implementations, the ring 104-*a* associated with the first user 102-*a* may be communicatively coupled to the user device 106-*a*, where the user device 106-*a* is communicatively coupled to the servers 110 via the network 108. In additional or alternative cases, wearable devices 104 (e.g., rings 104, watches 104) may be directly communicatively coupled to the network 108.

The system 100 may offer an on-demand database service between the user devices 106 and the one or more servers 110. In some cases, the servers 110 may receive data from the user devices 106 via the network 108, and may store and analyze the data. Similarly, the servers 110 may provide data to the user devices 106 via the network 108. In some cases, the servers 110 may be located at one or more data centers. The servers 110 may be used for data storage, management, and processing. In some implementations, the servers 110 may provide a web-based interface to the user device 106 via web browsers.

In some aspects, the system 100 may detect periods of time during which a user 102 is asleep, and classify periods of time during which the user 102 is asleep into one or more sleep stages (e.g., sleep stage classification). For example, as shown in FIG. 1, User 102-*a* may be associated with a wearable device 104-*a* (e.g., ring 104-*a*) and a user device 106-*a*. In this example, the ring 104-*a* may collect physiological data associated with the user 102-*a*, including temperature, heart rate, HRV, respiratory rate, and the like. In some aspects, data collected by the ring 104-*a* may be input to a machine learning classifier, where the machine learning classifier is configured to determine periods of time during which the user 102-*a* is (or was) asleep. Moreover, the machine learning classifier may be configured to classify periods of time into different sleep stages, including an awake sleep stage, a rapid eye movement (REM) sleep stage, a light sleep stage (non-REM (NREM)), and a deep sleep stage (NREM). In some aspects, the classified sleep stages may be displayed to the user 102-*a* via a GUI of the user device 106-*a*. Sleep stage classification may be used to provide feedback to a user 102-*a* regarding the user's sleeping patterns, such as recommended bedtimes, recommended wake-up times, and the like. Moreover, in some implementations, sleep stage classification techniques described herein may be used to calculate scores for the respective user, such as Sleep Scores, Readiness Scores, and the like.

In some aspects, the system 100 may utilize circadian rhythm-derived features to further improve physiological data collection, data processing procedures, and other techniques described herein. The term circadian rhythm may refer to a natural, internal process that regulates an individual's sleep-wake cycle, which repeats approximately every 24 hours. In this regard, techniques described herein may utilize circadian rhythm adjustment models to improve physiological data collection, analysis, and data processing. For example, a circadian rhythm adjustment model may be input into a machine learning classifier along with physiological data collected from the user 102-*a* via the wearable device 104-*a*. In this example, the circadian rhythm adjustment model may be configured to "weight," or adjust, physiological data collected throughout a user's natural, approximately 24-hour circadian rhythm. In some implementations, the system may initially start with a "baseline" circadian rhythm adjustment model, and may modify the baseline model using physiological data collected from each user 102 to generate tailored, individualized circadian rhythm adjustment models which are specific to each respective user 102.

In some aspects, the system 100 may utilize other biological rhythms to further improve physiological data collection, analysis, and processing by phase of these other rhythms. For example, if a weekly rhythm is detected within an individual's baseline data, then the model may be configured to adjust "weights" of data by day of the week. Biological rhythms that may require adjustment to the model by this method include: 1) ultradian (faster than a day rhythms, including sleep cycles in a sleep state, and oscillations from less than an hour to several hours periodicity in the measured physiological variables during wake state; 2) circadian rhythms; 3) non-endogenous daily rhythms shown to be imposed on top of circadian rhythms, as in work schedules; 4) weekly rhythms, or other artificial time periodicities exogenously imposed (e.g. in a hypothetical culture with 12 day "weeks", 12 day rhythms could be used); 5) multi-day ovarian rhythms in women and spermatogenesis rhythms in men; 6) lunar rhythms (relevant for individuals living with low or no artificial lights); and 7) seasonal rhythms.

The biological rhythms are not always stationary rhythms. For example, many women experience variability in ovarian cycle length across cycles, and ultradian rhythms are not expected to occur at exactly the same time or periodicity across days even within a user. As such, signal processing techniques sufficient to quantify the frequency composition while preserving temporal resolution of these rhythms in physiological data may be used to improve detection of these rhythms, to assign phase of each rhythm to each moment in time measured, and to thereby modify adjustment models and comparisons of time intervals. The biological rhythm-adjustment models and parameters can be added in linear or non-linear combinations as appropriate to more accurately capture the dynamic physiological baselines of an individual or group of individuals.

In some aspects, the respective devices of the system 100 may support techniques for menstrual cycle and ovarian cycle tracking based on data collected by a wearable device 104. In particular, the system 100 illustrated in FIG. 1 may support techniques for identifying one or more menstrual cycle phases of a user 102, and causing a user device 106 corresponding to the user 102 to display an indication of the identified one or more menstrual cycle phases. For example, as shown in FIG. 1, User 1 (user 102-*a*) may be associated with a wearable device 104-*a* (e.g., ring 104-*a*) and a user device 106-*a*. In this example, the ring 104-*a* may collect data associated with the user 102-*a*, including temperature, heart rate, respiratory rate, and the like. In some aspects, data collected by the ring 104-*a* may be used to identify one or more menstrual cycle phases (e.g., during which User 1 experiences a first day of a menstrual cycle, during which User 1 experiences ovulation, during which User 1 experiences an onset of the uterine cycle, and the like). Identifying the menstrual cycle phase be performed by any of the components of the system 100, including the ring 104-a, the user device 106-a associated with User 1, the one or more servers 110, or any combination thereof. Upon identifying the menstrual cycle phase, the system 100 may selectively cause the GUI of the user device 106-a to display an indication of the identified one or more menstrual cycle phases.

In some implementations, upon receiving physiological data (e.g., including temperature data), the system 100 may determine a time series of temperature values taken over a plurality of days. The system 100 may identify one or more morphological features of the time series of the plurality of temperature values. In such cases, the system 100 may identify the one or more menstrual cycle phases where each menstrual cycle phase of the one or more menstrual cycle phases is associated with a morphological feature in the time series. The morphological feature of the time series may include a negative slope, a positive slope, a minimum of the time series, a maximum of the times series, a deviation of the time series, or a combination thereof.

In some cases, the system 100 may prompt User 1 (e.g., via a GUI of the user device 106) to confirm whether the user 102-a experienced a first day of the menstrual cycle (e.g., menstruation) or not, and may selectively adjust Readiness Scores for the user 102-a based on confirmation that the user experienced a first day of the menstrual cycle. In some implementations, the system 100 may generate alerts, messages, or recommendations for User 1 (e.g., via the ring 104-a, user device 106-a, or both) based on the identified one or more menstrual cycle phases, where the alerts may provide insights regarding the identified menstrual cycle phases, such as a timing and/or duration of the identified menstrual cycle phases. In some cases, the messages may provide insight regarding symptoms associated with the identified menstrual cycle phases, one or more medical conditions associated with the identified menstrual cycle phases, educational videos and/or text (e.g., content) associated with the identified menstrual cycle phases, or a combination thereof related to any phase of the menstrual cycle.

It should be appreciated by a person skilled in the art that one or more aspects of the disclosure may be implemented in a system 100 to additionally or alternatively solve other problems than those described above. Furthermore, aspects of the disclosure may provide technical improvements to "conventional" systems or processes as described herein. However, the description and appended drawings only include example technical improvements resulting from implementing aspects of the disclosure, and accordingly do not represent all of the technical improvements provided within the scope of the claims.

Figure 2:
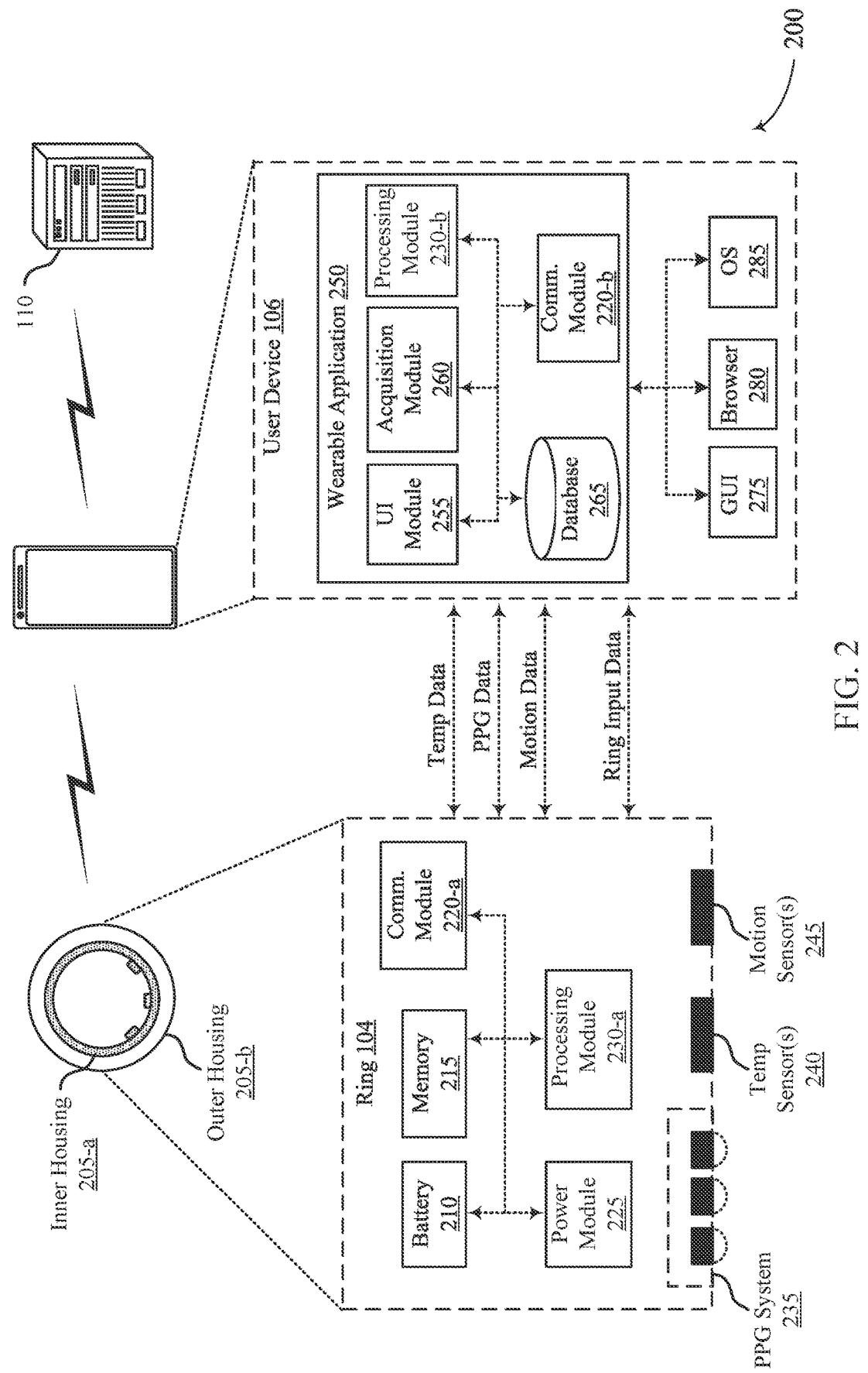
FIG. 2 illustrates an example of a system that supports menstrual cycle tracking in accordance with aspects of the present disclosure.

FIG. 2 illustrates an example of a system 200 that supports menstrual cycle tracking in accordance with aspects of the present disclosure. The system 200 may implement, or be implemented by, system 100. In particular, system 200 illustrates an example of a ring 104 (e.g., wearable device 104), a user device 106, and a server 110, as described with reference to FIG. 1.

In some aspects, the ring 104 may be configured to be worn around a user's finger, and may determine one or more user physiological parameters when worn around the user's finger. Example measurements and determinations may include, but are not limited to, user skin temperature, pulse waveforms, respiratory rate, heart rate, HRV, blood oxygen levels, and the like.

System 200 further includes a user device 106 (e.g., a smartphone) in communication with the ring 104. For example, the ring 104 may be in wireless and/or wired communication with the user device 106. In some implementations, the ring 104 may send measured and processed data (e.g., temperature data, photoplethysmogram (PPG) data, motion/accelerometer data, ring input data, and the like) to the user device 106. The user device 106 may also send data to the ring 104, such as ring 104 firmware/configuration updates. The user device 106 may process data. In some implementations, the user device 106 may transmit data to the server 110 for processing and/or storage.

The ring 104 may include a housing 205, which may include an inner housing 205-a and an outer housing 205-b. In some aspects, the housing 205 of the ring 104 may store or otherwise include various components of the ring including, but not limited to, device electronics, a power source (e.g., battery 210, and/or capacitor), one or more substrates (e.g., printable circuit boards) that interconnect the device electronics and/or power source, and the like. The device electronics may include device modules (e.g., hardware/software), such as: a processing module 230-a, a memory 215, a communication module 220-a, a power module 225, and the like. The device electronics may also include one or more sensors. Example sensors may include one or more temperature sensors 240, a PPG sensor assembly (e.g., PPG system 235), and one or more motion sensors 245.

The sensors may include associated modules (not illustrated) configured to communicate with the respective components/modules of the ring 104, and generate signals associated with the respective sensors. In some aspects, each of the components/modules of the ring 104 may be communicatively coupled to one another via wired or wireless connections. Moreover, the ring 104 may include additional and/or alternative sensors or other components which are configured to collect physiological data from the user, including light sensors (e.g., LEDs), oximeters, and the like.

The ring 104 shown and described with reference to FIG. 2 is provided solely for illustrative purposes. As such, the ring 104 may include additional or alternative components as those illustrated in FIG. 2. Other rings 104 that provide functionality described herein may be fabricated. For example, rings 104 with fewer components (e.g., sensors) may be fabricated. In a specific example, a ring 104 with a single temperature sensor 240 (or other sensor), a power source, and device electronics configured to read the single temperature sensor 240 (or other sensor) may be fabricated. In another specific example, a temperature sensor 240 (or other sensor) may be attached to a user's finger (e.g., using a clamps, spring loaded clamps, etc.). In this case, the sensor may be wired to another computing device, such as a wrist worn computing device that reads the temperature sensor 240 (or other sensor). In other examples, a ring 104 that includes additional sensors and processing functionality may be fabricated.

The housing 205 may include one or more housing 205 components. The housing 205 may include an outer housing 205-b component (e.g., a shell) and an inner housing 205-a component (e.g., a molding). The housing 205 may include additional components (e.g., additional layers) not explicitly illustrated in FIG. 2. For example, in some implementations, the ring 104 may include one or more insulating layers that electrically insulate the device electronics and other conductive materials (e.g., electrical traces) from the outer housing 205-*b* (e.g., a metal outer housing 205-*b*). The housing 205 may provide structural support for the device electronics, battery 210, substrate(s), and other components. For example, the housing 205 may protect the device electronics, battery 210, and substrate(s) from mechanical forces, such as pressure and impacts. The housing 205 may also protect the device electronics, battery 210, and substrate (s) from water and/or other chemicals.

The outer housing 205-*b* may be fabricated from one or more materials. In some implementations, the outer housing 205-*b* may include a metal, such as titanium, which may provide strength and abrasion resistance at a relatively light weight. The outer housing 205-*b* may also be fabricated from other materials, such polymers. In some implementations, the outer housing 205-*b* may be protective as well as decorative.

The inner housing 205-*a* may be configured to interface with the user's finger. The inner housing 205-*a* may be formed from a polymer (e.g., a medical grade polymer) or other material. In some implementations, the inner housing 205-*a* may be transparent. For example, the inner housing 205-*a* may be transparent to light emitted by the PPG light emitting diodes (LEDs). In some implementations, the inner housing 205-*a* component may be molded onto the outer housing 205-*b*. For example, the inner housing 205-*a* may include a polymer that is molded (e.g., injection molded) to fit into an outer housing 205-*b* metallic shell.

The ring 104 may include one or more substrates (not illustrated). The device electronics and battery 210 may be included on the one or more substrates. For example, the device electronics and battery 210 may be mounted on one or more substrates. Example substrates may include one or more printed circuit boards (PCBs), such as flexible PCB (e.g., polyimide). In some implementations, the electronics/battery 210 may include surface mounted devices (e.g., surface-mount technology (SMT) devices) on a flexible PCB. In some implementations, the one or more substrates (e.g., one or more flexible PCBs) may include electrical traces that provide electrical communication between device electronics. The electrical traces may also connect the battery 210 to the device electronics.

The device electronics, battery 210, and substrates may be arranged in the ring 104 in a variety of ways. In some implementations, one substrate that includes device electronics may be mounted along the bottom of the ring 104 (e.g., the bottom half), such that the sensors (e.g., PPG system 235, temperature sensors 240, motion sensors 245, and other sensors) interface with the underside of the user's finger. In these implementations, the battery 210 may be included along the top portion of the ring 104 (e.g., on another substrate).

The various components/modules of the ring 104 represent functionality (e.g., circuits and other components) that may be included in the ring 104. Modules may include any discrete and/or integrated electronic circuit components that implement analog and/or digital circuits capable of producing the functions attributed to the modules herein. For example, the modules may include analog circuits (e.g., amplification circuits, filtering circuits, analog/digital conversion circuits, and/or other signal conditioning circuits). The modules may also include digital circuits (e.g., combinational or sequential logic circuits, memory circuits etc.).

The memory 215 (memory module) of the ring 104 may include any volatile, non-volatile, magnetic, or electrical media, such as a random access memory (RAM), read-only memory (ROM), non-volatile RAM (NVRAM), electrically-erasable programmable ROM (EEPROM), flash memory, or any other memory device. The memory 215 may store any of the data described herein. For example, the memory 215 may be configured to store data (e.g., motion data, temperature data, PPG data) collected by the respective sensors and PPG system 235. Furthermore, memory 215 may include instructions that, when executed by one or more processing circuits, cause the modules to perform various functions attributed to the modules herein. The device electronics of the ring 104 described herein are only example device electronics. As such, the types of electronic components used to implement the device electronics may vary based on design considerations.

The functions attributed to the modules of the ring 104 described herein may be embodied as one or more processors, hardware, firmware, software, or any combination thereof. Depiction of different features as modules is intended to highlight different functional aspects and does not necessarily imply that such modules must be realized by separate hardware/software components. Rather, functionality associated with one or more modules may be performed by separate hardware/software components or integrated within common hardware/software components.

The processing module 230-*a* of the ring 104 may include one or more processors (e.g., processing units), microcontrollers, digital signal processors, systems on a chip (SOCs), and/or other processing devices. The processing module 230-*a* communicates with the modules included in the ring 104. For example, the processing module 230-*a* may transmit/receive data to/from the modules and other components of the ring 104, such as the sensors. As described herein, the modules may be implemented by various circuit components. Accordingly, the modules may also be referred to as circuits (e.g., a communication circuit and power circuit).

The processing module 230-*a* may communicate with the memory 215. The memory 215 may include computer-readable instructions that, when executed by the processing module 230-*a*, cause the processing module 230-*a* to perform the various functions attributed to the processing module 230-*a* herein. In some implementations, the processing module 230-*a* (e.g., a microcontroller) may include additional features associated with other modules, such as communication functionality provided by the communication module 220-*a* (e.g., an integrated Bluetooth Low Energy transceiver) and/or additional onboard memory 215.

The communication module 220-*a* may include circuits that provide wireless and/or wired communication with the user device 106 (e.g., communication module 220-*b* of the user device 106). In some implementations, the communication modules 220-*a*, 220-*b* may include wireless communication circuits, such as Bluetooth circuits and/or Wi-Fi circuits. In some implementations, the communication modules 220-*a*, 220-*b* can include wired communication circuits, such as Universal Serial Bus (USB) communication circuits. Using the communication module 220-*a*, the ring 104 and the user device 106 may be configured to communicate with each other. The processing module 230-*a* of the ring may be configured to transmit/receive data to/from the user device 106 via the communication module 220-*a*. Example data may include, but is not limited to, motion data, temperature data, pulse waveforms, heart rate data, HRV data, PPG data, and status updates (e.g., charging status, battery charge level, and/or ring 104 configuration settings). The processing module 230-*a* of the ring may also be configured to receive updates (e.g., software/firmware updates) and data from the user device 106.

The ring 104 may include a battery 210 (e.g., a rechargeable battery 210). An example battery 210 may include a Lithium-Ion or Lithium-Polymer type battery 210, although a variety of battery 210 options are possible. The battery 210 may be wirelessly charged. In some implementations, the ring 104 may include a power source other than the battery 210, such as a capacitor. The power source (e.g., battery 210 or capacitor) may have a curved geometry that matches the curve of the ring 104. In some aspects, a charger or other power source may include additional sensors which may be used to collect data in addition to, or which supplements, data collected by the ring 104 itself. Moreover, a charger or other power source for the ring 104 may function as a user device 106, in which case the charger or other power source for the ring 104 may be configured to receive data from the ring 104, store and/or process data received from the ring 104, and communicate data between the ring 104 and the servers 110.

In some aspects, the ring 104 includes a power module 225 that may control charging of the battery 210. For example, the power module 225 may interface with an external wireless charger that charges the battery 210 when interfaced with the ring 104. The charger may include a datum structure that mates with a ring 104 datum structure to create a specified orientation with the ring 104 during 104 charging. The power module 225 may also regulate voltage(s) of the device electronics, regulate power output to the device electronics, and monitor the state of charge of the battery 210. In some implementations, the battery 210 may include a protection circuit module (PCM) that protects the battery 210 from high current discharge, over voltage during 104 charging, and under voltage during 104 discharge. The power module 225 may also include electro-static discharge (ESD) protection.

The one or more temperature sensors 240 may be electrically coupled to the processing module 230-*a*. The temperature sensor 240 may be configured to generate a temperature signal (e.g., temperature data) that indicates a temperature read or sensed by the temperature sensor 240. The processing module 230-*a* may determine a temperature of the user in the location of the temperature sensor 240. For example, in the ring 104, temperature data generated by the temperature sensor 240 may indicate a temperature of a user at the user's finger (e.g., skin temperature). In some implementations, the temperature sensor 240 may contact the user's skin. In other implementations, a portion of the housing 205 (e.g., the inner housing 205-*a*) may form a barrier (e.g., a thin, thermally conductive barrier) between the temperature sensor 240 and the user's skin. In some implementations, portions of the ring 104 configured to contact the user's finger may have thermally conductive portions and thermally insulative portions. The thermally conductive portions may conduct heat from the user's finger to the temperature sensors 240. The thermally insulative portions may insulate portions of the ring 104 (e.g., the temperature sensor 240) from ambient temperature.

In some implementations, the temperature sensor 240 may generate a digital signal (e.g., temperature data) that the processing module 230-*a* may use to determine the temperature. As another example, in cases where the temperature sensor 240 includes a passive sensor, the processing module 230-*a* (or a temperature sensor 240 module) may measure a current/voltage generated by the temperature sensor 240 and determine the temperature based on the measured current/voltage. Example temperature sensors 240 may include a thermistor, such as a negative temperature coefficient (NTC) thermistor, or other types of sensors including resistors, transistors, diodes, and/or other electrical/electronic components.

The processing module 230-*a* may sample the user's temperature over time. For example, the processing module 230-*a* may sample the user's temperature according to a sampling rate. An example sampling rate may include one sample per second, although the processing module 230-*a* may be configured to sample the temperature signal at other sampling rates that are higher or lower than one sample per second. In some implementations, the processing module 230-*a* may sample the user's temperature continuously throughout the day and night. Sampling at a sufficient rate (e.g., one sample per second) throughout the day may provide sufficient temperature data for analysis described herein.

The processing module 230-*a* may store the sampled temperature data in memory 215. In some implementations, the processing module 230-*a* may process the sampled temperature data. For example, the processing module 230-*a* may determine average temperature values over a period of time. In one example, the processing module 230-*a* may determine an average temperature value each minute by summing all temperature values collected over the minute and dividing by the number of samples over the minute. In a specific example where the temperature is sampled at one sample per second, the average temperature may be a sum of all sampled temperatures for one minute divided by sixty seconds. The memory 215 may store the average temperature values over time. In some implementations, the memory 215 may store average temperatures (e.g., one per minute) instead of sampled temperatures in order to conserve memory 215.

The sampling rate, which may be stored in memory 215, may be configurable. In some implementations, the sampling rate may be the same throughout the day and night. In other implementations, the sampling rate may be changed throughout the day/night. In some implementations, the ring 104 may filter/reject temperature readings, such as large spikes in temperature that are not indicative of physiological changes (e.g., a temperature spike from a hot shower). In some implementations, the ring 104 may filter/reject temperature readings that may not be reliable due to other factors, such as excessive motion during 104 exercise (e.g., as indicated by a motion sensor 245).

The ring 104 (e.g., communication module) may transmit the sampled and/or average temperature data to the user device 106 for storage and/or further processing. The user device 106 may transfer the sampled and/or average temperature data to the server 110 for storage and/or further processing.

Although the ring 104 is illustrated as including a single temperature sensor 240, the ring 104 may include multiple temperature sensors 240 in one or more locations, such as arranged along the inner housing 205-*a* near the user's finger. In some implementations, the temperature sensors 240 may be stand-alone temperature sensors 240. Additionally, or alternatively, one or more temperature sensors 240 may be included with other components (e.g., packaged with other components), such as with the accelerometer and/or processor.

The processing module 230-*a* may acquire and process data from multiple temperature sensors 240 in a similar manner described with respect to a single temperature sensor 240. For example, the processing module 230 may individually sample, average, and store temperature data from each of the multiple temperature sensors 240. In other examples, the processing module 230-*a* may sample the sensors at different rates and average/store different values for the different sensors. In some implementations, the processing module 230-*a* may be configured to determine a single temperature based on the average of two or more temperatures determined by two or more temperature sensors 240 in different locations on the finger.

The temperature sensors 240 on the ring 104 may acquire distal temperatures at the user's finger (e.g., any finger). For example, one or more temperature sensors 240 on the ring 104 may acquire a user's temperature from the underside of a finger or at a different location on the finger. In some implementations, the ring 104 may continuously acquire distal temperature (e.g., at a sampling rate). Although distal temperature measured by a ring 104 at the finger is described herein, other devices may measure temperature at the same/different locations. In some cases, the distal temperature measured at a user's finger may differ from the temperature measured at a user's wrist or other external body location. Additionally, the distal temperature measured at a user's finger (e.g., a "shell" temperature) may differ from the user's core temperature. As such, the ring 104 may provide a useful temperature signal that may not be acquired at other internal/external locations of the body. In some cases, continuous temperature measurement at the finger may capture temperature fluctuations (e.g., small or large fluctuations) that may not be evident in core temperature. For example, continuous temperature measurement at the finger may capture minute-to-minute or hour-to-hour temperature fluctuations that provide additional insight that may not be provided by other temperature measurements elsewhere in the body.

The ring 104 may include a PPG system 235. The PPG system 235 may include one or more optical transmitters that transmit light. The PPG system 235 may also include one or more optical receivers that receive light transmitted by the one or more optical transmitters. An optical receiver may generate a signal (hereinafter "PPG" signal) that indicates an amount of light received by the optical receiver. The optical transmitters may illuminate a region of the user's finger. The PPG signal generated by the PPG system 235 may indicate the perfusion of blood in the illuminated region. For example, the PPG signal may indicate blood volume changes in the illuminated region caused by a user's pulse pressure. The processing module 230-*a* may sample the PPG signal and determine a user's pulse waveform based on the PPG signal. The processing module 230-*a* may determine a variety of physiological parameters based on the user's pulse waveform, such as a user's respiratory rate, heart rate, HRV, oxygen saturation, and other circulatory parameters.

In some implementations, the PPG system 235 may be configured as a reflective PPG system 235 in which the optical receiver(s) receive transmitted light that is reflected through the region of the user's finger. In some implementations, the PPG system 235 may be configured as a transmissive PPG system 235 in which the optical transmitter(s) and optical receiver(s) are arranged opposite to one another, such that light is transmitted directly through a portion of the user's finger to the optical receiver(s).

The number and ratio of transmitters and receivers included in the PPG system 235 may vary. Example optical transmitters may include light-emitting diodes (LEDs). The optical transmitters may transmit light in the infrared spectrum and/or other spectrums. Example optical receivers may include, but are not limited to, photosensors, phototransistors, and photodiodes. The optical receivers may be configured to generate PPG signals in response to the wavelengths received from the optical transmitters. The location of the transmitters and receivers may vary. Additionally, a single device may include reflective and/or transmissive PPG systems 235.

The PPG system 235 illustrated in FIG. 2 may include a reflective PPG system 235 in some implementations. In these implementations, the PPG system 235 may include a centrally located optical receiver (e.g., at the bottom of the ring 104) and two optical transmitters located on each side of the optical receiver. In this implementation, the PPG system 235 (e.g., optical receiver) may generate the PPG signal based on light received from one or both of the optical transmitters. In other implementations, other placements, combinations, and/or configurations of one or more optical transmitters and/or optical receivers are contemplated.

The processing module 230-*a* may control one or both of the optical transmitters to transmit light while sampling the PPG signal generated by the optical receiver. In some implementations, the processing module 230-*a* may cause the optical transmitter with the stronger received signal to transmit light while sampling the PPG signal generated by the optical receiver. For example, the selected optical transmitter may continuously emit light while the PPG signal is sampled at a sampling rate (e.g., 250 Hz).

Sampling the PPG signal generated by the PPG system 235 may result in a pulse waveform, which may be referred to as a "PPG." The pulse waveform may indicate blood pressure vs time for multiple cardiac cycles. The pulse waveform may include peaks that indicate cardiac cycles. Additionally, the pulse waveform may include respiratory induced variations that may be used to determine respiration rate. The processing module 230-*a* may store the pulse waveform in memory 215 in some implementations. The processing module 230-*a* may process the pulse waveform as it is generated and/or from memory 215 to determine user physiological parameters described herein.

The processing module 230-*a* may determine the user's heart rate based on the pulse waveform. For example, the processing module 230-*a* may determine heart rate (e.g., in beats per minute) based on the time between peaks in the pulse waveform. The time between peaks may be referred to as an interbeat interval (IBI). The processing module 230-*a* may store the determined heart rate values and IBI values in memory 215.

The processing module 230-*a* may determine HRV over time. For example, the processing module 230-*a* may determine HRV based on the variation in the IBIs. The processing module 230-*a* may store the HRV values over time in the memory 215. Moreover, the processing module 230-*a* may determine the user's respiratory rate over time. For example, the processing module 230-*a* may determine respiratory rate based on frequency modulation, amplitude modulation, or baseline modulation of the user's IBI values over a period of time. Respiratory rate may be calculated in breaths per minute or as another breathing rate (e.g., breaths per 30 seconds). The processing module 230-*a* may store user respiratory rate values over time in the memory 215.

The ring 104 may include one or more motion sensors 245, such as one or more accelerometers (e.g., 6-D accelerometers) and/or one or more gyroscopes (gyros). The motion sensors 245 may generate motion signals that indicate motion of the sensors. For example, the ring 104 may include one or more accelerometers that generate acceleration signals that indicate acceleration of the accelerometers. As another example, the ring 104 may include one or more gyro sensors that generate gyro signals that indicate angular motion (e.g., angular velocity) and/or changes in orientation. The motion sensors 245 may be included in one or more sensor packages. An example accelerometer/gyro sensor is a Bosch BM1160 inertial micro electro-mechanical system (MEMS) sensor that may measure angular rates and accelerations in three perpendicular axes.

The processing module 230-a may sample the motion signals at a sampling rate (e.g., 50 Hz) and determine the motion of the ring 104 based on the sampled motion signals. For example, the processing module 230-a may sample acceleration signals to determine acceleration of the ring 104. As another example, the processing module 230-a may sample a gyro signal to determine angular motion. In some implementations, the processing module 230-a may store motion data in memory 215. Motion data may include sampled motion data as well as motion data that is calculated based on the sampled motion signals (e.g., acceleration and angular values).

The ring 104 may store a variety of data described herein. For example, the ring 104 may store temperature data, such as raw sampled temperature data and calculated temperature data (e.g., average temperatures). As another example, the ring 104 may store PPG signal data, such as pulse waveforms and data calculated based on the pulse waveforms (e.g., heart rate values, IBI values, HRV values, and respiratory rate values). The ring 104 may also store motion data, such as sampled motion data that indicates linear and angular motion.

The ring 104, or other computing device, may calculate and store additional values based on the sampled/calculated physiological data. For example, the processing module 230 may calculate and store various metrics, such as sleep metrics (e.g., a Sleep Score), activity metrics, and readiness metrics. In some implementations, additional values/metrics may be referred to as "derived values." The ring 104, or other computing/wearable device, may calculate a variety of values/metrics with respect to motion. Example derived values for motion data may include, but are not limited to, motion count values, regularity values, intensity values, metabolic equivalence of task values (METs), and orientation values. Motion counts, regularity values, intensity values, and METs may indicate an amount of user motion (e.g., velocity/acceleration) over time. Orientation values may indicate how the ring 104 is oriented on the user's finger and if the ring 104 is worn on the left hand or right hand.

In some implementations, motion counts and regularity values may be determined by counting a number of acceleration peaks within one or more periods of time (e.g., one or more 30 second to 1 minute periods). Intensity values may indicate a number of movements and the associated intensity (e.g., acceleration values) of the movements. The intensity values may be categorized as low, medium, and high, depending on associated threshold acceleration values. METs may be determined based on the intensity of movements during a period of time (e.g., 30 seconds), the regularity/irregularity of the movements, and the number of movements associated with the different intensities.

In some implementations, the processing module 230-a may compress the data stored in memory 215. For example, the processing module 230-a may delete sampled data after making calculations based on the sampled data. As another example, the processing module 230-a may average data over longer periods of time in order to reduce the number of stored values. In a specific example, if average temperatures for a user over one minute are stored in memory 215, the processing module 230-a may calculate average temperatures over a five minute time period for storage, and then subsequently erase the one minute average temperature data. The processing module 230-a may compress data based on a variety of factors, such as the total amount of used/available memory 215 and/or an elapsed time since the ring 104 last transmitted the data to the user device 106.

Although a user's physiological parameters may be measured by sensors included on a ring 104, other devices may measure a user's physiological parameters. For example, although a user's temperature may be measured by a temperature sensor 240 included in a ring 104, other devices may measure a user's temperature. In some examples, other wearable devices (e.g., wrist devices) may include sensors that measure user physiological parameters. Additionally, medical devices, such as external medical devices (e.g., wearable medical devices) and/or implantable medical devices, may measure a user's physiological parameters. One or more sensors on any type of computing device may be used to implement the techniques described herein.

The physiological measurements may be taken continuously throughout the day and/or night. In some implementations, the physiological measurements may be taken during 104 portions of the day and/or portions of the night. In some implementations, the physiological measurements may be taken in response to determining that the user is in a specific state, such as an active state, resting state, and/or a sleeping state. For example, the ring 104 can make physiological measurements in a resting/sleep state in order to acquire cleaner physiological signals. In one example, the ring 104 or other device/system may detect when a user is resting and/or sleeping and acquire physiological parameters (e.g., temperature) for that detected state. The devices/systems may use the resting/sleep physiological data and/or other data when the user is in other states in order to implement the techniques of the present disclosure.

In some implementations, as described previously herein, the ring 104 may be configured to collect, store, and/or process data, and may transfer any of the data described herein to the user device 106 for storage and/or processing. In some aspects, the user device 106 includes a wearable application 250, an operating system (OS), a web browser application (e.g., web browser 280), one or more additional applications, and a GUI 275. The user device 106 may further include other modules and components, including sensors, audio devices, haptic feedback devices, and the like. The wearable application 250 may include an example of an application (e.g., "app") which may be installed on the user device 106. The wearable application 250 may be configured to acquire data from the ring 104, store the acquired data, and process the acquired data as described herein. For example, the wearable application 250 may include a user interface (UI) module 255, an acquisition module 260, a processing module 230-b, a communication module 220-b, and a storage module (e.g., database 265) configured to store application data.

The various data processing operations described herein may be performed by the ring 104, the user device 106, the servers 110, or any combination thereof. For example, in some cases, data collected by the ring 104 may be preprocessed and transmitted to the user device 106. In this example, the user device 106 may perform some data processing operations on the received data, may transmit the data to the servers 110 for data processing, or both. For instance, in some cases, the user device 106 may perform processing operations which require relatively low processing power and/or operations which require a relatively low latency, whereas the user device 106 may transmit the data to the servers 110 for processing operations which require relatively high processing power and/or operations which may allow relatively higher latency.

In some aspects, the ring 104, user device 106, and server 110 of the system 200 may be configured to evaluate sleep patterns for a user. In particular, the respective components of the system 200 may be used to collect data from a user via the ring 104, and generate one or more scores (e.g., Sleep Score, Readiness Score) for the user based on the collected data. For example, as noted previously herein, the ring 104 of the system 200 may be worn by a user to collect data from the user, including temperature, heart rate, HRV, and the like. Data collected by the ring 104 may be used to determine when the user is asleep in order to evaluate the user's sleep for a given "sleep day." In some aspects, scores may be calculated for the user for each respective sleep day, such that a first sleep day is associated with a first set of scores, and a second sleep day is associated with a second set of scores. Scores may be calculated for each respective sleep day based on data collected by the ring 104 during the respective sleep day. Scores may include, but are not limited to, Sleep Scores, Readiness Scores, and the like.

In some cases, "sleep days" may align with the traditional calendar days, such that a given sleep day runs from midnight to midnight of the respective calendar day. In other cases, sleep days may be offset relative to calendar days. For example, sleep days may run from 6:00 pm (18:00) of a calendar day until 6:00 pm (18:00) of the subsequent calendar day. In this example, 6:00 pm may serve as a "cut-off time," where data collected from the user before 6:00 pm is counted for the current sleep day, and data collected from the user after 6:00 pm is counted for the subsequent sleep day. Due to the fact that most individuals sleep the most at night, offsetting sleep days relative to calendar days may enable the system 200 to evaluate sleep patterns for users in such a manner which is consistent with their sleep schedules. In some cases, users may be able to selectively adjust (e.g., via the GUI) a timing of sleep days relative to calendar days so that the sleep days are aligned with the duration of time in which the respective users typically sleep.

In some implementations, each overall score for a user for each respective day (e.g., Sleep Score, Readiness Score) may be determined/calculated based on one or more "contributors," "factors," or "contributing factors." For example, a user's overall Sleep Score may be calculated based on a set of contributors, including: total sleep, efficiency, restfulness, REM sleep, deep sleep, latency, timing, or any combination thereof. The Sleep Score may include any quantity of contributors. The "total sleep" contributor may refer to the sum of all sleep periods of the sleep day. The "efficiency" contributor may reflect the percentage of time spent asleep compared to time spent awake while in bed, and may be calculated using the efficiency average of long sleep periods (e.g., primary sleep period) of the sleep day, weighted by a duration of each sleep period. The "restfulness" contributor may indicate how restful the user's sleep is, and may be calculated using the average of all sleep periods of the sleep day, weighted by a duration of each period. The restfulness contributor may be based on a "wake up count" (e.g., sum of all the wake-ups (when user wakes up) detected during different sleep periods), excessive movement, and a "got up count" (e.g., sum of all the got-ups (when user gets out of bed) detected during the different sleep periods).

The "REM sleep" contributor may refer to a sum total of REM sleep durations across all sleep periods of the sleep day including REM sleep. Similarly, the "deep sleep" contributor may refer to a sum total of deep sleep durations across all sleep periods of the sleep day including deep sleep. The "latency" contributor may signify how long (e.g., average, median, longest) the user takes to go to sleep, and may be calculated using the average of long sleep periods throughout the sleep day, weighted by a duration of each period and the number of such periods (e.g., consolidation of a given sleep stage or sleep stages may be its own contributor or weight other contributors). Lastly, the "timing" contributor may refer to a relative timing of sleep periods within the sleep day and/or calendar day, and may be calculated using the average of all sleep periods of the sleep day, weighted by a duration of each period.

By way of another example, a user's overall Readiness Score may be calculated based on a set of contributors, including: sleep, sleep balance, heart rate, HRV balance, recovery index, temperature, activity, activity balance, or any combination thereof. The Readiness Score may include any quantity of contributors. The "sleep" contributor may refer to the combined Sleep Score of all sleep periods within the sleep day. The "sleep balance" contributor may refer to a cumulative duration of all sleep periods within the sleep day. In particular, sleep balance may indicate to a user whether the sleep that the user has been getting over some duration of time (e.g., the past two weeks) is in balance with the user's needs. Typically, adults need 7-9 hours of sleep a night to stay healthy, alert, and to perform at their best both mentally and physically. However, it is normal to have an occasional night of bad sleep, so the sleep balance contributor takes into account long-term sleep patterns to determine whether each user's sleep needs are being met. The "resting heart rate" contributor may indicate a lowest heart rate from the longest sleep period of the sleep day (e.g., primary sleep period) and/or the lowest heart rate from naps occurring after the primary sleep period.

Continuing with reference to the "contributors" (e.g., factors, contributing factors) of the Readiness Score, the "HRV balance" contributor may indicate a highest HRV average from the primary sleep period and the naps happening after the primary sleep period. The HRV balance contributor may help users keep track of their recovery status by comparing their HRV trend over a first time period (e.g., two weeks) to an average HRV over some second, longer time period (e.g., three months). The "recovery index" contributor may be calculated based on the longest sleep period. Recovery index measures how long it takes for a user's resting heart rate to stabilize during the night. A sign of a very good recovery is that the user's resting heart rate stabilizes during the first half of the night, at least six hours before the user wakes up, leaving the body time to recover for the next day. The "body temperature" contributor may be calculated based on the longest sleep period (e.g., primary sleep period) or based on a nap happening after the longest sleep period if the user's highest temperature during the nap is at least 0.5° C. higher than the highest temperature during the longest period. In some aspects, the ring may measure a user's body temperature while the user is asleep, and the system 200 may display the user's average temperature relative to the user's baseline temperature. If a user's body temperature is outside of their normal range (e.g., clearly above or below 0.0), the body temperature contributor may be highlighted (e.g., go to a "Pay attention" state) or otherwise generate an alert for the user.

In some aspects, the system 200 may support techniques for menstrual cycle tracking. In particular, the respective components of the system 200 may be used to identify one or more menstrual cycle phases in a time series representing the user's temperature over time. The menstrual cycle phase for the user may be predicted by leveraging temperature sensors on the ring 104 of the system 200. In some cases, the menstrual cycle phase may be estimated by identifying one or more morphological features such as negative slopes of the time series representing the user's temperature over time and identifying the one or more menstrual cycle phases that correspond to the morphological features of the time series. The menstrual cycle phase may include a stage of menstruation, a stage of the ovarian cycle, a stage of the uterine cycle, or a combination thereof.

For example, as noted previously herein, the ring 104 of the system 200 may be worn by a user to collect data from the user, including temperature, heart rate, respiratory data, and the like. The ring 104 of the system 200 may collect the physiological data from the user based temperature sensors and measurements extracted from arterial blood flow. The physiological data may be collected continuously. In some implementations, the processing module 230-a may sample the user's temperature continuously throughout the day and night. Sampling at a sufficient rate (e.g., one sample per second) throughout the day and/or night may provide sufficient temperature data for analysis described herein. In some implementations, the ring 104 may continuously acquire temperature data (e.g., at a sampling rate). In some examples, even though temperature is collected continuously, the system 200 may leverage other information about the user that it has collected or otherwise derived (e.g., sleep stage, activity levels, illness onset, etc.) to select a representative temperature for a particular day that is an accurate representation of the underlying physiological phenomenon. In contrast, systems that require a user to manually take their temperature each day and/or systems that measure temperature continuously but lack any other contextual information about the user may select inaccurate or inconsistent temperature values for their menstrual cycle predictions, leading to inaccurate predictions and decreased user experience. In contrast, data collected by the ring 104 may be used to accurately determine when the user experiences a first day of menstruation, a first day of ovulation, or any day throughout menstruation, ovulation, and the uterine cycle. Identified menstrual cycle phases and related techniques are further shown and described with reference to FIG. 3.

Figure 3:
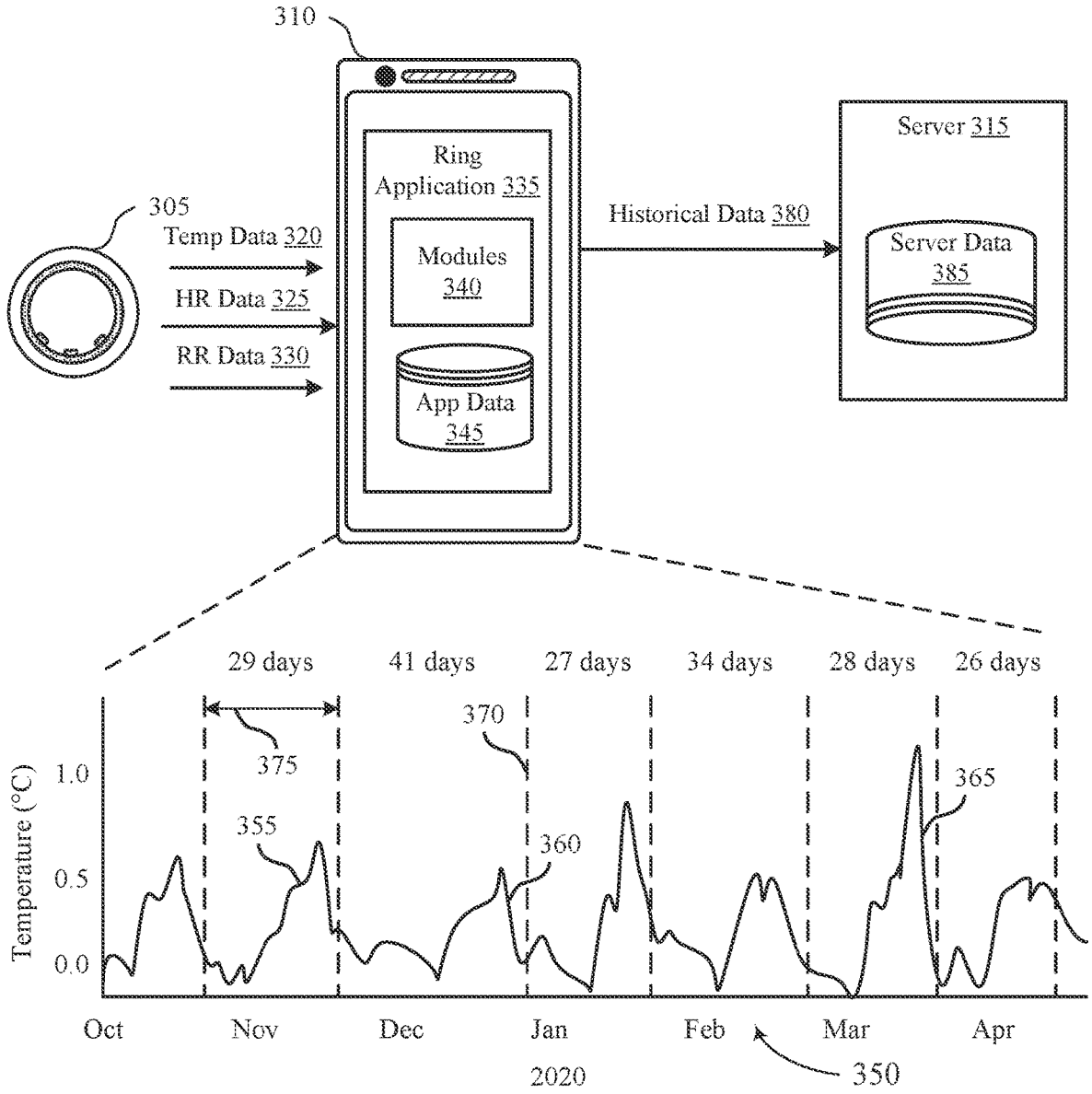
FIG. 3 illustrates an example of a system that supports menstrual cycle tracking in accordance with aspects of the present disclosure.

FIG. 3 illustrates an example of a system 300 that supports menstrual cycle tracking in accordance with aspects of the present disclosure. The system 300 may implement, or be implemented by, system 100, system 200, or both. In particular, system 300 illustrates an example of a ring 104 (e.g., wearable device 104), a user device 106, and a server 110, as described with reference to FIG. 1.

The ring 305 may acquire temperature data 320, heart rate data 325, and respiratory data 330. In such cases, the ring 305 may transmit temperature data 320, heart rate data 325, and respiratory data 330 to the user device 310. The temperature data 320 may include continuous nighttime temperature data, continuous daytime temperature data, or both. In some cases, multiple devices may acquire physiological data. For example, a first computing device (e.g., user device 310) and a second computing device (e.g., the ring 305) may acquire temperature data 320, heart rate data 325, respiratory data 330, or a combination thereof.

For example, the ring 305 may acquire user physiological data, such as user temperature data 320, respiratory rate data 330, heart rate data 325, HRV, galvanic skin response, blood oxygen saturation, actigraphy, and/or other user physiological data. The ring 305 may send the data to another computing device, such as a mobile device (e.g., user device 310) for further processing. For example, the user device 310 may determine menstrual/ovarian/uterine cycle tracking data based on the received data. In some cases, the system 300 may determine menstrual cycle tracking data based on temperature data 320, respiratory rate data 330, heart rate data 325, HRV, galvanic skin response, blood oxygen saturation, activity, sleep architecture, or a combination thereof. Although the system may be implemented by a ring 305 and a user device 310, any combination of computing devices described herein may implement the features attributed to the system 300.

The user device 310 may include a ring application 335. The ring application 335 may include at least modules 340 and application data 345. In some cases, the application data 345 may include historical temperature patterns for the user and other data. The other data may include temperature data 320, heart rate data 325, respiratory data 330, or a combination thereof.

The ring application 335 may present identified menstrual cycle phases to the user. The ring application 335 may include an application data processing module that may perform data processing. For example, the application data processing module may include modules 340 that provide functions attributed to the system 300. Example modules 340 may include a daily temperature determination module, a time series processing module, and a menstrual cycle module. The daily temperature determination module may determine daily temperature values (e.g., by selecting a representative temperature value for that day from a series of temperature values that were collected continuously throughout the day and/or night). The time series processing module may process time series data to detect menstrual cycle onset events (e.g., menstrual cycle phases). The menstrual cycle module may identify menstrual cycle phases (e.g., period onset events, a stage of the menstrual cycle, ovarian cycle, and uterine cycle, or a combination thereof) based on the processed time series data. The ring application 335 may store application data 345, such as acquired temperature data, other physiological data, and cycle tracking data (e.g., event data).

In some cases, the system 300 may generate cycle tracking data (e.g., menstrual cycle phases) based on user physiological data (e.g., temperature data) 320 and/or motion data. The cycle tracking data may include period onset data (e.g., menstrual cycle phases 370), which may be determined based on acquired user temperature data (e.g., daily temperature data 320) over an analysis time period (e.g., a period of weeks/months). For example, the system 300 may receive physiological data associated with a user from a wearable device (e.g., ring 305). The physiological data may include at least temperature data 320, heart rate data 325, respiratory data 330, or a combination thereof. For example, the system 300 acquires user physiological data over an analysis time period (e.g., a plurality of days). In such cases, the system 300 may acquire and process user physiological data over an analysis time period to generate one or more time series 350 of user physiological data.

In some cases, the system 300 may acquire daily user temperature data 320 over an analysis time period. For example, the system 300 may calculate a single temperature value for each day. The system 300 may acquire a plurality of temperature values 355 during the day/night and process the acquired temperature values 355 to determine the single daily temperature value. In some implementations, the system 300 may determine a time series 350 of a plurality of temperature values 355 taken over a plurality of days based at least in part on the received temperature data 320. In the illustrated example, the time series 350 may include a plurality of days that ranges from October through April. The time series 350 may include the plurality of temperature values 355, menstrual cycle phases 370 (e.g., dashed vertical lines), and at least a period length 375 for a user, as described herein. In some cases, the time series 350 may include a luteal phase length, a follicular phase length, an ovulation phase length, or a combination thereof.

In some cases, the system 300 may analyze the time series 350 (e.g., time series data) over the analysis time period to determine menstrual cycle tracking data, which may include menstrual cycle phases 370 (e.g., approximately monthly phases). A plurality of temperature values 355 over the analysis time period (e.g., weeks or months) may form a time series 350 of temperature values 355 that may be processed. In some cases, the system may process the time series 350 of daily temperature values 355 to identify changes in temperature values 355 that may indicate menstrual cycle phases 370.

In some examples, the system 300 may determine a time series 350 of daily temperature values 355 over an analysis time period based on nighttime temperatures acquired by the ring 305. The system 300 may determine the derivative of the time series data. For example, the system may identify one or more morphological features 360 of the time series 350 of the plurality of temperature values 355 based on determining the time series 350. The time series 350 may include a plurality of menstrual cycles for the user (e.g., including a period length 375 of the menstrual cycle and/or a menstrual cycle phase 370). In some cases, the system 300 may process the time series 350 to smooth the data of the time series 350 (e.g., using a rolling average).

The system 300 may identify one or more of the maximum negative (e.g. steepest) slopes 365 in the time series 350 subject to time constraints (e.g., total times between slopes 360). For example, the system 300 may identify one or more maximum negative slopes 365 of the time series 350 of the plurality of temperature values 355 based on identifying the one or more morphological features 360. In such cases, each menstrual cycle phase 370 of the one or more menstrual cycle phases is associated with a maximum negative slope 365. For example, the system 300 may identify the period onsets (e.g., menstrual cycle phase 370) in the time series 350 as maximum negative (e.g., steepest downward) slopes 365. As such, the system 300 may identify menstrual cycle phases 370 in the time series 350 as places in the time series 350 associated with morphological features 360.

In some cases, the system 300 may identify the menstrual cycle phase 370 and in response, identify the period onset day (e.g., menstruation onset day). In some examples, the system 300 may identify the menstrual cycle phase 370 and in response, identify the ovulation onset day, a length of ovulation, a length of the uterine cycle, a length of the follicular phase, a length of the luteal phase, or a combination thereof based on identifying the menstrual cycle phase 370.

The system 300 may identify one or more menstrual cycle phases 370 in the time series 350 based on identifying the one or more morphological features 360 of the time series 350. In such cases, each menstrual cycle phase 370 of the one or more menstrual cycle phases is associated with a morphological feature 360 in the time series 350. The system 300 may determine menstrual cycle tracking data for the time series 350 based on changes in temperature. For example, the system 300 may identify menstrual cycle phases 370 based on temperature slopes (e.g., temperature drops) in the time series 350 of temperature values 355. The system 300 may identify menstrual cycle phases 370 based on temperature increases (e.g., positive slopes), temperature deviations from a temperature baseline of the user, or both.

In some implementations, the system 300 may determine that the received heart rate data 325 satisfies a threshold for at least a portion of the plurality of days. In such cases, the system 300 may identify the one or more menstrual cycle phases 370 in the time series 350 based on determining that the received heart rate data 325 satisfies the threshold. In some examples, the system 300 may determine that the received respiratory rate data 330 satisfies a threshold for at least a portion of the plurality of days. In such cases, the system 300 may identify the one or more menstrual cycle phases 370 in the time series 350 based on determining that the received respiratory rate data 330 satisfies the threshold. The threshold may be an example of a baseline of the user (e.g., a heart rate baseline, a respiratory rate baseline, etc.).

The system 300 may cause a GUI of the user device 310 to display the identified one or more menstrual cycle phases 370. In some cases, the system 300 may cause the GUI to display the time series 350. The system 300 may generate menstrual cycle tracking data output. For example, the system 300 may generate a tracking GUI that includes physiological data (e.g., temperature data 320), tagged events, and/or other GUI elements described herein with reference to FIG. 7. In such cases, the system 300 may render menstrual cycle phases 370 in a menstrual cycle tracking GUI.

In some implementations, the ring application 335 may notify the user of identified menstrual cycle phases and/or prompt the user to perform a variety of tasks in the activity GUI. For example, notifications may notify the user of a recently identified menstrual cycle phase 370. In some examples, a prompt may request confirmation by the user. The notifications and prompts may include text, graphics, and/or other user interface elements. The notifications and prompts may be included in the ring application 335 such as when there is a menstrual cycle phase 370 that has just been identified, the ring application 335 may display notifications and prompts. The user device 310 may display notifications and prompts in a separate window on the home screen and/or overlaid onto other screens (e.g., at the very top of the home screen). In some cases, the user device 310 may display the notifications and prompts on a mobile device, a user's watch device, or both.

In some implementations, the user device 310 may store historical user data. In some cases, the historical user data may include historical data 380. The historical data 380 may include historical temperature patterns of the user, historical heart rate patterns of the user, historical respiratory rate patterns of the user, historical menstrual cycle phases (e.g., period length, menstruation start date, ovulation length, etc.) of the user, or a combination thereof. The historical data 380 may be used (e.g., by the user device 310 or server 315) to select a portion of a sleep period for a user, determine temperature values of the user, identify menstrual cycle phases, or a combination thereof. The historical data 380 may be used by the server 315. Using the historical data 380 may allow the user device 310 and/or server 315 to personalize the GUI by taking into consideration user's historical data 380.

In such cases, the user device 310 may transmit historical data 380 to the server 315. In some cases, the transmitted historical data 380 may be the same historical data stored in the ring application 335. In other examples, the historical data 380 may be different than the historical data stored in the ring application 335. The server 315 may receive the historical data 380. The server 315 may store the historical data 380 in server data 385.

In some implementations, the user device 310 and/or server 315 may also store other data which may be an example of user information. The user information may include, but is not limited to, user age, weight, height, and gender. In some implementations, the user information may be used as features for identifying menstrual cycle phases. The server data 385 may include the other data such as user information.

Figure 4:
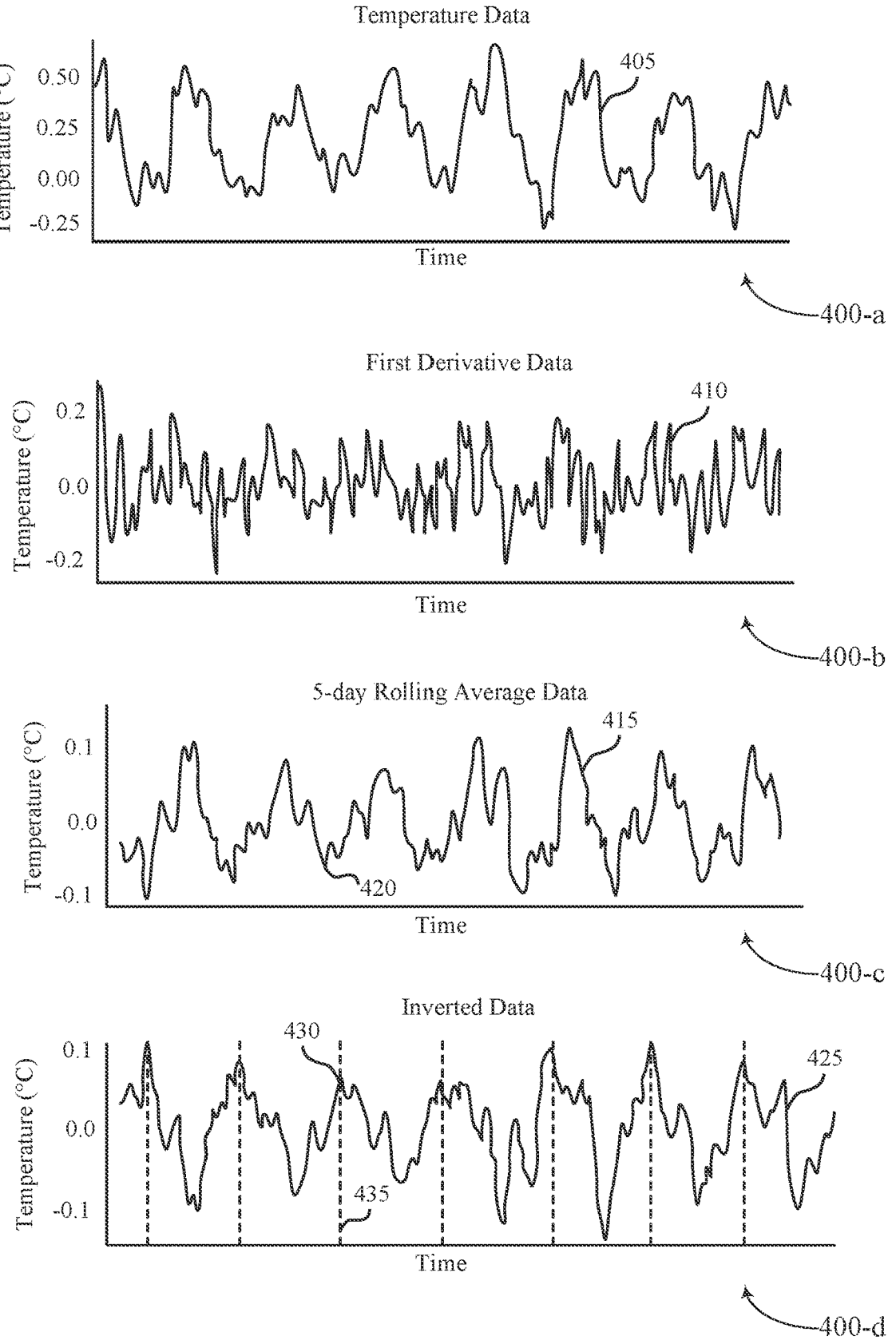
FIG. 4 illustrates an example of timing diagrams that supports menstrual cycle tracking in accordance with aspects of the present disclosure.

FIG. 4 illustrates an example of timing diagrams 400 that support menstrual cycle tracking in accordance with aspects of the present disclosure. The timing diagrams 400 may implement, or be implemented by, aspects of the system 100, system 200, system 300, or a combination thereof. For example, in some implementations, the timing diagrams 400 may be displayed to a user via the GUI 275 of the user device 106, as shown in FIG. 2.

As described in further detail herein, the system may be configured to track menstrual cycles including menstruation, ovulation cycles, and uterine cycles. In some cases, the user's core body temperature pattern throughout the day and night may be an indicator that may characterize a phase of the menstrual cycle. For example, skin temperature during the day and night may identify a menstrual cycle phase. As such, the timing diagram 400-*a* illustrates a relationship between a user's temperature data and a time (e.g., over a plurality of days and/or months). In this regard, the solid curved line illustrated in the timing diagram 400-*a* may be understood to refer to the "temperature values 405." The user's temperature values 405 may be relative to a baseline temperature.

In some cases, the system (e.g., ring 104, user device 106, server 110) may receive physiological data associated with a user from a wearable device. The physiological data may include at least temperature data. The system may determine a time series of a plurality of temperature values 405 taken over a plurality of days based on the received temperature data. With reference to timing diagram 400-*a*, the plurality of days may be an example of 7 months. The system may process original time series temperature data (e.g., temperature values 405) to determine what stage of the three-stage menstrual cycle (e.g., menstruation, ovarian, uterine) that the user is currently in. In such cases, the time series may include a plurality of menstrual cycles for the user.

The temperature values 405 may be continuously collected by the wearable device. The physiological measurements may be taken continuously throughout the day and/or night. For example, in some implementations, the ring may be configured to acquire physiological data (e.g., temperature data, sleep data, heart rate, MET data, and the like) continuously in accordance with one or more measurement periodicities throughout the entirety of each day/sleep day. In other words, the ring may continuously acquire physiological data from the user without regard to "trigger conditions" for performing such measurements. In some cases, continuous temperature measurement at the finger may capture temperature fluctuations (e.g., small or large fluctuations) that may not be evident in core temperature. For example, continuous temperature measurement at the finger may capture minute-to-minute or hour-to-hour temperature fluctuations that provide additional insight that may not be provided by other temperature measurements elsewhere in the body or if the user were manually taking their temperature once per day.

In some cases, the system may identify one or more morphological features of the time series of the plurality of temperature values 405 after determining the time series. The system may identify one or more menstrual cycle phases in the time series of temperature values 405 in response to identifying the one or more morphological features of the time series. For example, each menstrual cycle phase of the one or more menstrual cycle phases is associated with a morphological feature in the time series of temperature values 405.

In some cases, the system may determine, or estimate, the temperature maximum and/or minimum for a user after determining the time series of the temperature values 405 for the user collected via the ring. The system may identify the one or more morphological features of the time series of the plurality of temperature values 405 based on determining the maximum and/or minimum. In some cases, calculating the difference between the maximum and minimum may determine the morphological feature (e.g., slope). In other examples, identify the one or more morphological features of the time series of the plurality of temperature values 405 may be in response to computing the derivative of the original time series temperature data (e.g., temperature values 405).

The timing diagram 400-*b* illustrates a relationship between a user's temperature data and a time (e.g., over a plurality of days and/or months). In this regard, the solid curved line illustrated in the timing diagram 400-*b* may be understood to refer to the "derivative temperature values 410." With reference to timing diagram 400-*b*, the plurality of days may be an example of 7 months.

The system may determine a first derivative of the original data of temperature values 405. For example, the system may compute a derivative of the time series of the plurality of temperatures values 405. The computed derivative of the time series of the plurality of temperature values 405 may be an example of the derivative temperature values 410. In some cases, the system may identify one or more local maximum or one or more local minimum of the derivative of the time series (e.g., derivative temperature values 410). In such cases, each menstrual cycle phase of the one or more of menstrual cycle phases may be associated with the one or more local maximum or the one or more local minimum of the derivative of the time series. The slope of the temperature values 405 may correspond to (e.g., be an example of) the derivative temperature values 410.

The timing diagram 400-*c* illustrates a relationship between a user's temperature data and a time (e.g., over a plurality of days and/or months). In this regard, the solid curved line illustrated in the timing diagram 400-*c* may be understood to refer to the "average derivative temperature values 415." With reference to timing diagram 400-*c*, the plurality of days may be an example of 7 months.

The system may smooth the data of the derivative temperature values 410 by taking a five-day rolling average. In some cases, the system may identify one or more local maximum or one or more local minimum 420 of the average derivative temperature values 415. In such cases, each menstrual cycle phase of the one or more of menstrual cycle phases may be associated with the one or more local maximum or the one or more local minimum of the average derivative temperature values 415. The slope of the temperature values 405 may correspond to (e.g., be an example of) the average derivative temperature values 415.

The timing diagram 400-*d* illustrates a relationship between a user's temperature data and a time (e.g., over a plurality of days and/or months). In this regard, the solid curved line illustrated in the timing diagram 400-*d* may be understood to refer to the "inverted temperature values 425." In this regard, the vertical broken lines illustrated in the timing diagram 400-*d* may be understood to refer to the "menstrual cycle phase 435." The user's temperature data may be relative to a baseline temperature. With reference to timing diagram 400-*d*, the plurality of days may be an example of 7 months.

The system may invert the data to find peaks within distances of greater than 21 days. The peaks may be identified as period onset dates (e.g., menstrual cycle phases). For example, the system may invert the derivative of the time series of the plurality of temperatures (e.g., derivative temperature values 410 and/or average derivative temperature values 415) in response to computing the derivative of the time series. The system may identify one or more local maximum 430 of the inverted derivative of the time series (e.g., inverted temperature data 425). In such cases, each menstrual cycle phase 435 of the one or more menstrual cycle phases may be associated with the one or more local maximum 430 of the inverted derivative of the time series (e.g., inverted temperature data 425).

Figure 5:
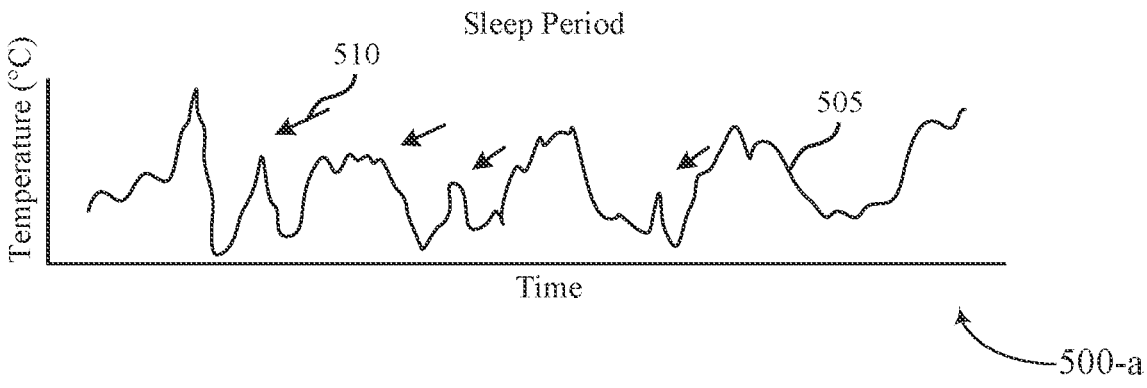
FIG. 5 illustrates an example of a timing diagram that supports menstrual cycle tracking in accordance with aspects of the present disclosure.
Figure 5:
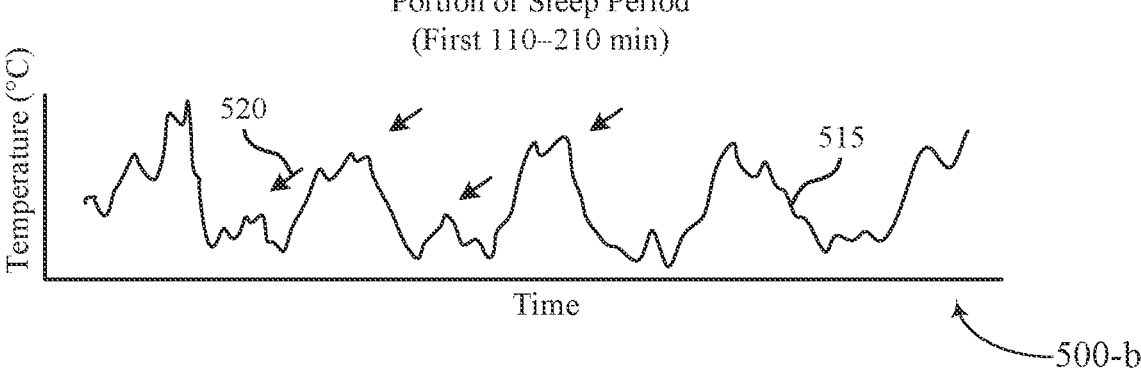
Figure 5:
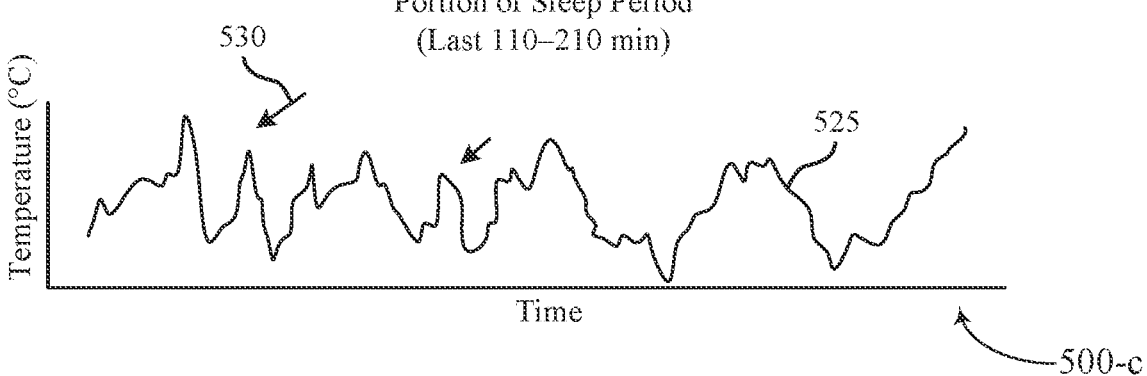

FIG. 5 illustrates an example of timing diagrams 500 that support menstrual cycle tracking in accordance with aspects of the present disclosure. The timing diagrams 500 may implement, or be implemented by, aspects of the system 100, system 200, system 300, or a combination thereof. For example, in some implementations, the timing diagrams 500 may be displayed to a user via the GUI 275 of the user device 106, as shown in FIG. 2.

In some implementations, the system may acquire user temperature from specific phases of the sleep period in order to refine the cyclical pattern, allow for greater accuracy in detection of specific points along the menstrual cycle, or segment users into categories with relevance for fertility, reproductive aging, perimenopausal transitions, and hormonal or behavioral treatments. For example, with respect to timing diagrams 500, the system may determine a primary nightly temperature trend deviation variable. In such cases, the system may determine a cyclical menstrual pattern.

As described in further detail herein, the system may be configured to track menstrual cycles and identify a phase of the menstrual cycle that the user is experiencing (e.g., menstruation, ovulation, or the uterine cycle). In some cases, the user's core body temperature pattern throughout the night may be an indicator that may characterize the menstrual cycle. For example, skin temperature during the night may identify a menstrual cycle phase. As such, the timing diagram 500-*a* illustrates a relationship between a user's temperature data and a time (e.g., a single night and/or over a plurality of days). In this regard, the solid curved line illustrated in the timing diagram 500-*a* may be understood to refer to the "temperature values 505."

In some cases, the system (e.g., ring 104, user device 106, server 110) may receive physiological data associated with a user from a wearable device. The physiological data may include at least continuous nighttime temperature data. The system may determine a time series of a plurality of temperature values 505 taken over a plurality of days based on the received continuous nighttime temperature data. With reference to timing diagram 500-*a*, the time period may be a sleep period over the course of a single night.

The temperature values 505 may be continuously collected by the wearable device. The physiological measurements may be taken continuously throughout the night. For example, in some implementations, the ring may be configured to acquire physiological data (e.g., temperature data, sleep data, heart rate, MET data, and the like) continuously in accordance with one or more measurement periodicities throughout the entirety of each sleep day. In other words, the ring may continuously acquire physiological data from the user without regard to "trigger conditions" for performing such measurements. In some cases, continuous temperature measurement at the finger may capture temperature fluctuations (e.g., small or large fluctuations) that may not be evident in core temperature. For example, continuous temperature measurement at the finger may capture minute-to-minute or hour-to-hour temperature fluctuations that provide additional insight that may not be provided by other temperature measurements elsewhere in the body or if the user were manually taking their temperature once per day.

The system may identify a sleep period of the user based on determining the time series of the plurality of temperature values 505. The system may identify one or more local maximums 510 of the temperature values 505 throughout the entire sleep period. In some cases, the system may determine each temperature value of the plurality of temperature values 505 in response to receiving the temperature data. In such cases, the temperature data may include continuous nighttime temperature data. In other examples, the temperature data may include continuous daytime temperature data.

The timing diagram 500-*b* illustrates a relationship between a user's temperature data and a time (e.g., over a single night and/or plurality of days). In this regard, the solid curved line illustrated in the timing diagram 500-*b* may be understood to refer to the "early temperature values 515." With reference to timing diagram 500-*b*, the time period may be a portion of the sleep period. For example, the portion of the sleep period may be the first 110-210 minutes of the user's sleep.

The system may select a portion of the sleep period of the user. In such cases, the system may select a first portion of the sleep period that includes early temperature values 515 of the sleep period. In some cases, identifying the one or more morphological features of the time series of the plurality of temperature values may be based on selecting the first portion of the sleep period. In some examples, the system may select a portion of a sleep period of the user based on historical temperature patterns for the user. In such cases, determining each temperature value of the plurality of temperature values may be based on selecting the portion of the sleep period. The system may identify one or more local maximums 520 of the early temperature values 515 throughout the first portion of the sleep period. In this way, the system may be able to select a representative temperature for a particular day by leveraging other information about the user that provides context about that temperature value (e.g., that the representative temperature value is selected from an early phase of sleep, or a later phase of sleep, or a specific sleep stage, etc.), which is an advantage over systems that lack such additional contextual information and just blindly select a maximum or average temperature for an entire day.

The timing diagram 500-*c* illustrates a relationship between a user's temperature data and a time (e.g., over a single night and/or plurality of days). In this regard, the solid curved line illustrated in the timing diagram 500-*c* may be understood to refer to the "late temperature values 525." With reference to timing diagram 500-*c*, the time period may be a portion of the sleep period. For example, the portion of the sleep period may be the last 110-210 minutes of the user's sleep.

The system may select a portion of the sleep period of the user. In such cases, the system may select a second portion of the sleep period that includes late temperature values 525 of the sleep period. In some cases, identifying the one or more morphological features of the time series of the plurality of temperature values may be based on selecting the second portion of the sleep period. In some examples, the system may select a portion of a sleep period of the user based on historical temperature patterns for the user. In such cases, determining each temperature value of the plurality of late temperature values may be based on selecting the portion of the sleep period. The system may identify one or more local maximums 530 of the late temperature values 525 throughout the second portion of the sleep period.

The timing diagram 500-b may plot the second max or high quantile (e.g., 99th) taken from the early portion of the evening (first 110-210 min after falling asleep). In contrast, timing diagram 500-a and timing diagram 500-c may include occasional smaller peaks that occur as the temperature drops. Because finding peaks and the largest drops in temperature may be features for a detection algorithm in the system, acquiring the best accuracy at scale across a broad range of users with different hormonal and circadian rhythms may be enhanced by taking temperature from different portions of the sleep period. The smaller peaks (e.g., local maximums 510, 520, 530) may be a physiologically relevant feature for cycle-detection by the system, as it may correspond to a sympathetically-mediated splanchnic nerve pulse that helps motivate the awakening response and send input to the ovaries and reproductive system.

In some implementations, the system may take the local maximums 510, 520, 530 temperature for every 30 minute interval (after signal processing steps) and then extract the second maximum of those 30 minute average values. In some cases, the highest temperatures (e.g., local maximum 520) may occur in the early portion of sleep (e.g., in the first 110-210 minutes). In other examples, the highest temperature (e.g., local maximum 530) may occur in the later portion of the evening. By extracting the 99th % quantile or second max temperature in the first 110-210 minutes after falling asleep (e.g., early temperature values 515) or the last 110-210 minutes before waking up (e.g., late temperature values 525), the system may obtain more granular information.

Obtaining granular information based on selecting a portion of the sleep period may allow for personalization by using the metric that is most appropriate for a given user (e.g., one who tends to have the highest temperatures only in the early evening). Obtaining granular information may also allow for precision reproductive medicine. Users with a more exaggerated smaller bump (e.g., local maximums) in-between the evident cycles may have differences in their luteal surge. Quantifying the smaller peak (e.g., local maximum 530) using late temperature values 525 may help predict fertility windows. Obtaining granular information may also allow for generalizability at scale by allowing predictions across substantial variability in age and birth control or exogenous hormone effects. For example, progesterone treatments may increase temperatures across the night and blunt cycling.

In some cases, the system may acquire different temperature values when extracting temperature metrics from the early portion of sleep or the late portion of sleep. In some cases, during the early portion of sleep, as described with reference to timing diagram 500-b, the user's early temperature values 515 may include a pattern of heat in the first sleep cycle (e.g., first 110 min) which may drive the ability to detect the menstrual cycle. In such cases, the user may experience high early temperatures values 515. In some implementations, the system may detect this pattern of heat by taking a user's max, second-max, or a high quantile of a statistical distribution across the early portion of the sleep period (e.g., relative to bedtime). In some implementations, the system may detect this pattern of heat by finding the half hour period throughout the night with the highest average early temperature values 515 and determining which users the max occurs in the early portion of the evening.

In some cases, the menstrual cycles and temperature patterns may be different from one user to another. The differences in temperature patterns (e.g., the overall heat, the timing of relative highs and lows temperatures, and the ultradian rhythms) may be used to identify subgroups of users and personalize the system (e.g., personalize determination of daily temperatures).

In some implementations, the system may capture the temperature data by employing features based on statistical distributions of temperature or slopes of change in temperature from the early to late sleep period. In some implementations, algorithms may base the timing of features on chronologic time. In some examples, timing may be anchored to a user's bedtime on a particular night and the timing of different sleep stages detected, such as REM sleep, non-REM sleep, or deep sleep. In some implementations, the system may extract ultradian rhythms of temperature during the night and use the peak timing, prominence, width, and other signal processing features as features for personalizing the algorithm.

In some cases, the temperature data may vary for users experiencing a perimenopause transition (e.g., users 45-55 years of age). Perimenopause may represent the tail end of a woman's reproductive journey, and may therefore not be separate from cycle detection, but is the end phase of that reproductive trajectory with age. The system may allow for detection of menstrual cycle irregularity, which may be quantified through distributions of cycle lengths or measures of variance, such as the standard deviation or interquartile range. Age-related cycle irregularity may be associated with a depleted ovarian reserve, lower Anti-Mullerian Hormone (AMH) levels, high Follicle Stimulating Hormone (FSH) levels, and/or diminished follicle quality (predictors of fertility treatment success). In such cases, the system may identify a loss of the typical high temperatures concentrated in the early portion of the sleep period.

In some implementations, the system may determine metrics related to cycle length and irregularity to the user, potentially in comparison to age-bracketed norms, in order to provide users with personalized information relevant to their reproductive health. In some implementations, the system may use metrics related to age-adjusted shortened cycle lengths, regularity, and/or general patterning in order to classify users who may be more likely to benefit from certain kinds of fertility/perimenopausal treatments, such as intrauterine insemination (IUD, in vitro fertilization (IVF), or hormone replacement therapy (HRT) protocols, or behavioral interventions, such as the use and timing of melatonin, CBD, or HRV biofeedback prior to bedtime.

The system may implement a variety of models and algorithms to implement the features described herein. For example, the system may implement neural networks, image analysis, prospective prediction algorithms, and/or subgroup detection and clustering for precision medicine/personalized insights. In some implementations, the system may use alternative algorithms to detect the timing of the menstrual period. For example, the system may take heatmaps and feed the heatmaps into a convolutional neural network (CNN), auto-encoder, or various deep learning approaches appropriate for image analysis, and then feed the subsequent features into a time series detection model.

In some implementations, the system may use various temperature features, such as the temperature distributions, their ultradian rhythms, or their timing relative to bedtime, sleep staging, or phase of sleep (early, late, etc.) to predict a user's next period start date. In some implementations, the system may use various temperature features to cluster users into subgroups. For example, the system may apply various machine learning clustering algorithms, such as factor analysis, principal components, K-means, K-nearest neighbors, or agglomerative clustering or more in order to assign users to a subgroup. The subgroups may provide the basis for personalized insights in the ring application. For example, the system may be able to detect users using different kinds of birth control, users with various reproductive-related conditions like premature ovarian aging or endometriosis, or detect the impact of pharmacotherapy on menstrual or ovarian cycling.

In some implementations, the system may use other signals combined with temperature. For example, the system may combine information from a variety of other sensors and signals to improve the detection or prediction of the phase of a user's cycle, or the timing of various cycle-related events. In one example, the system may include features or frequency extractions from a PPG signal or actigraphy sensors and activity detection among others. In some implementations, the system may use HRV features. For example, various heart rate and HRV features can be derived from a PPG, which can be useful in cycle detection. The system may extract a variety of HRV frequency bands and features, such as the root mean squared difference between successive intervals (RMSSD), the high frequency (HF), low frequency (LF), very low frequency (VLF), and respiration rate frequencies (BR for breathing rate to distinguish from the RR interval in a PPG signal). The system may extract peak power in a given frequency range measured over appropriate intervals during the night (e.g., approximately 1 minute for HF, approximately 5 minutes for LF, etc.). The system may use these frequency based features to strengthen a cycle-phase detection or prediction algorithm. In some implementations, the system may extract the coherence between the cyclic patterns of various HRV features and temperature cycles in order to strengthen cycle-phase detection or prediction algorithms.

In some cases, the RMSSD HRV signal, or the coherence of RMSSD with temperature during sleep may be an additional feature used for the system to help detect or predict inter-cycle variability. Definitive peaks in the coherence of RMSSD with high temperatures during sleep may correspond with the peaks of estradiol, luteinizing hormone (LH), or follicle-stimulating hormone (FSH), which are relevant to identifying the timing of ovulation, understanding cycle-irregularity, predicting fertility success, and understanding reproductive aging. In some implementations, the HF component of HRV derived from PPG, and its nadirs, may reflect a withdrawal of parasympathetic input to the reproductive system, which may serve as a marker or correlate for the drops in estradiol and/or progesterone, which precede period onset. Accordingly, features in the time or frequency domain, related to the rhythmicity of HF, LF, RMSSD, VLF, respiration rate, or other HRV measures may contribute to detection or prediction of subsequent period start times and other relevant phases of the menstrual or ovarian cycles.

Figure 6:
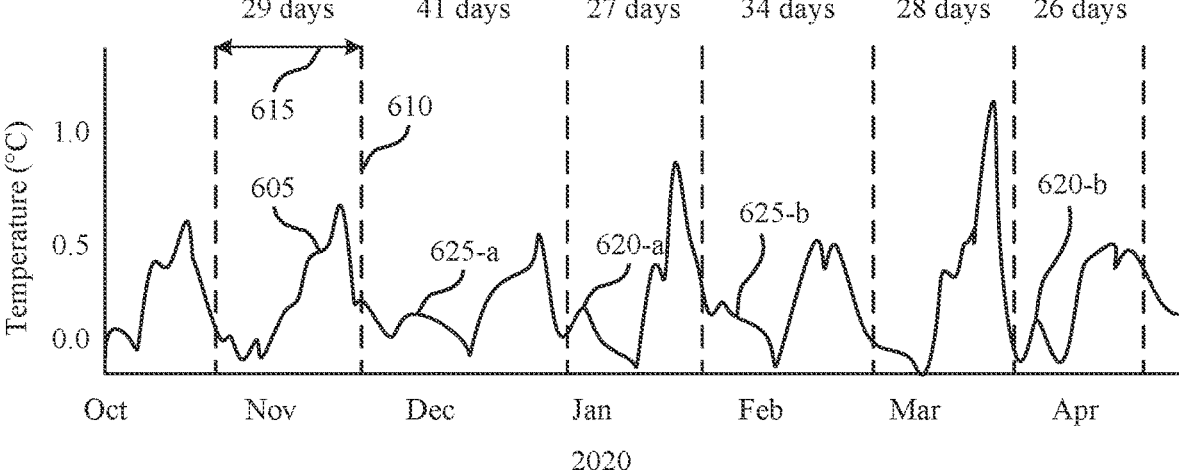
FIG. 6 illustrates an example of a timing diagram that supports menstrual cycle tracking in accordance with aspects of the present disclosure.

FIG. 6 illustrates an example of a timing diagram 600 that supports menstrual cycle tracking in accordance with aspects of the present disclosure. The timing diagram 600 may implement, or be implemented by, aspects of the system 100, system 200, system 300, or a combination thereof. For example, in some implementations, the timing diagram 600 may be displayed to a user via the GUI 275 of the user device 106, as shown in FIG. 2.

The system may track menstrual/ovarian/uterine events based on additional/alternative time series morphology. In some implementations, the system may identify secondary peaks (e.g., lesser bumps) or lower local maximums that sometimes occur between the major temperature peaks and may have additional relevance to cycle-phase identification. For example, with reference to timing diagram 600, for users with irregular periods, the system may use morphological features of the temperature time series to detect or predict shorter and longer menstrual cycle lengths than a user's median, average, or typical cycle-length. In some examples, the system may alert user when the system identifies a lower local maximum 620 (sharper bump) in the temperature following a menstrual cycle phase 610. The identification of lower local maximum 620 may indicate that the next period onset day may come earlier than usual (e.g., 26 and 27 day cycles).

In other examples, when a lower local maximum 625 (e.g., flatter bump) that appears long and flat in the temperature values 605 that follow a menstrual cycle phase 610, the system may alert a user that the next period onset day could be coming later than usual (e.g., 41 to 34 day cycles). A lower local maximum 620 or 625 may also be detected by temperature features derived from specific times of the night (e.g., early sleep period versus late sleep period). For example, late-sleep high temperatures may include a lower local maximum 620 or secondary peak that follows menstruation start than early-sleep high temperatures.

Later in the evening, the splanchnic nervous system may send sympathetic pulses that affect the circadian rhythms and help regulate the reproductive and thermoregulatory systems. The withdrawal of estrogen, which may occur during the menstrual cycle, and may be more pronounced in older users, may alter noradrenergic and serotonergic signaling. The system may use the prominence, width, timing, or other morphological characteristics of the temperature values 605 over the course of a cycle to provide a set of features or proxy biomarkers to detect and predict different phases of the menstrual/ovarian cycle. For example, temperature curves that show a lower local maximum 620 or 625 in the two to five days following a menstrual cycle phase 610, which may also be detectable later in the sleep period, may provide a proxy marker with applications for predicting more irregular cycles. Such morphological features may reflect the coordination of thermoregulatory, sympathetic, and reproductive systems, and thereby serve as proxy markers for reproductive health diseases or conditions associated with deficits of these systems, which may be used to analyze reproductive health.

In some implementations, the system may detect other events in the menstrual cycle (e.g., other than menstrual cycle phases 610). For example, a lower local maximum 620 or 625, pronounced in the late-sleep period, may be relevant to quantifying the length of the period (e.g., cycle length 615), the inter-cycle variability within the window of fertility, the timing of the LH surge, and/or the timing of ovulation. In some cases, a lower local maximum 620 or 625 may correlate to variability in FSH which may be seen in timing diagram 600 as the lower local maximum 620 that follows shortly after the beginning of the period (e.g., menstrual cycle phases 610), as detected in temperature values 605.

For example, the system may identify additional menstrual cycle events in response to determining the time series of the plurality of temperature values 605. In such cases, the system may identify ovarian cycle events during the plurality of days based on the time series of the plurality of temperature values 605, heart rate data, respiratory rate data, or both. The system may estimate a future menstrual cycle phase 610 during which the user experiences a first day of menstruation based on the time series of the plurality of temperature values 605, the identified one or more menstrual cycle phases 610, or both. In some cases, the system may estimate a length of the user's current menstrual cycle (e.g., cycle length 615) based on a morphology of the time series of the plurality of temperature values 605 after a previous menstrual cycle phase 610.

In some implementations, the system may use user-reported period dates (e.g., collected in the ring application) combined with the temperature-based period onset time series to generate a metric of cycle irregularity for an individual user. For example, the system may compute a metric of irregularity using statistical or machine learning quantifications of a distribution, such as the standard deviation, interquartile range, spread of the distribution, kurtosis/skewness parameters, the coefficient of dispersion, matrix-profile based irregularity, and absolute values or squared differences of the time series of estimated period start dates. In some cases, temperature cycle irregularity may be a likely biomarker that user's reproductive cycles are entering or approaching the perimenopausal transition.

The user-reported period dates may be overlaid with the identified and/or predicted menstrual cycle phases 610. The system may be validated and improved based on actual user identified menstrual cycle phases. For example, the tracking algorithms may be personalized for individual users based on how well their actual period onsets match with the system estimated onsets or how well their ovulation matches with the system estimated ovulation. In some cases, the actual period onsets and/or ovulation may be within zero to three days of the estimated onsets.

Figure 7:
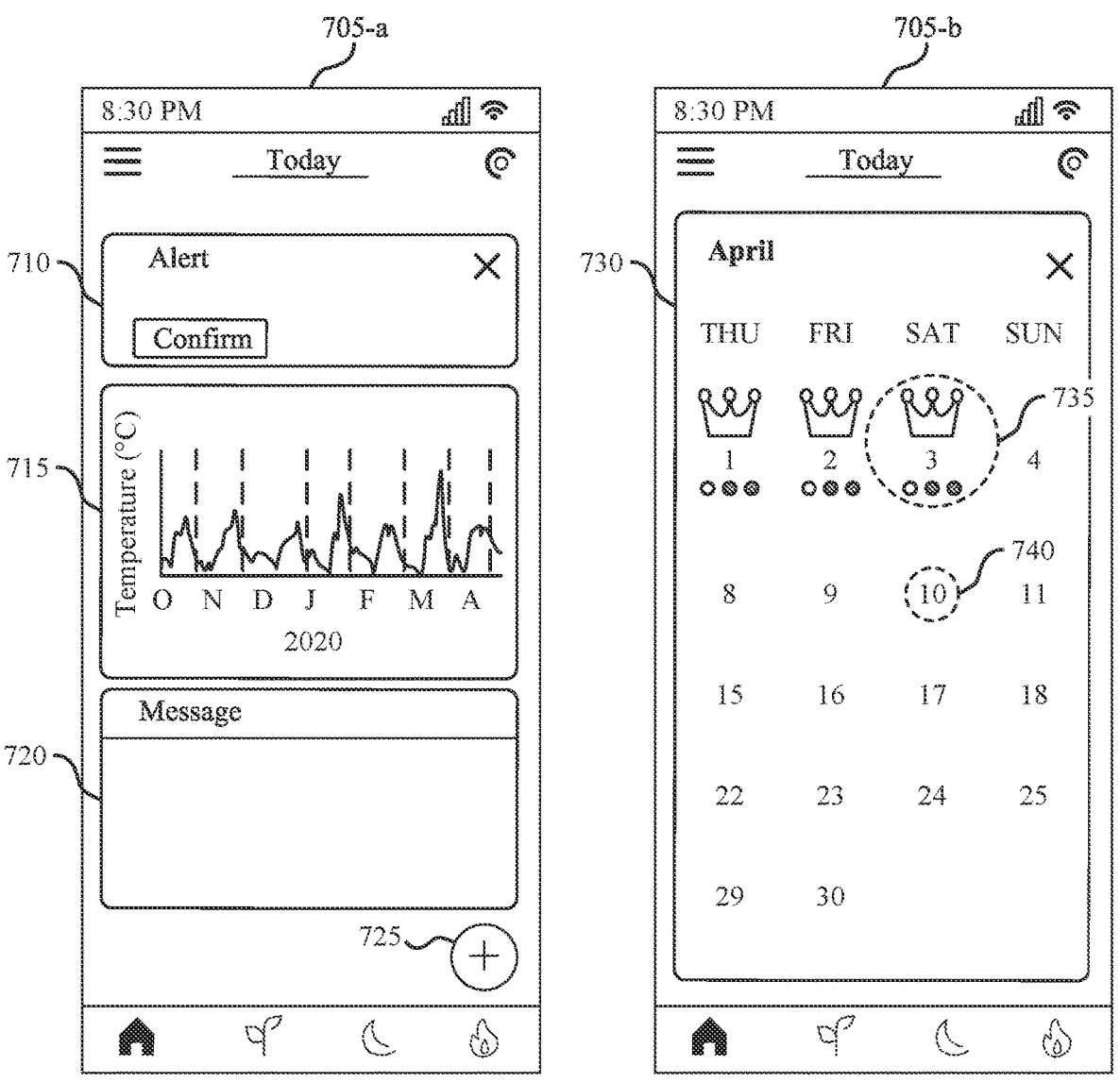
FIG. 7 illustrates an example of a graphical user interface (GUI) that supports menstrual cycle tracking in accordance with aspects of the present disclosure.

FIG. 7 illustrates an example of a GUI 700 that supports menstrual cycle tracking in accordance with aspects of the present disclosure. The GUI 700 may implement, or be implemented by, aspects of the system 100, system 200, system 300, timing diagram 400, timing diagram 500, timing diagram 600, or any combination thereof. For example, the GUI 700 may be an example of a GUI 275 of a user device 106 (e.g., user device 106-*a*, 106-*b*, 106-*c*) corresponding to a user 102.

In some examples, the GUI 700 illustrates a series of application pages 705 which may be displayed to a user via the GUI 700 (e.g., GUI 275 illustrated in FIG. 2). The server of the system may cause the GUI 700 of the user device (e.g., mobile device) to display inquiries of whether the user activates the period mode and wants to track their menstrual cycle (e.g., via application page 705). In such cases, the system may generate a personalized cycle tracking experience on the GUI 700 of the user device to identify a menstrual cycle phase based on the contextual tags and user questions.

Continuing with the examples above, prior to identifying a menstrual cycle phase, the user may be presented with an application page upon opening the wearable application. The application page 705 may display a request to activate the period mode, ovulation mode, and the like and enable the system to track the menstrual cycle. In such cases, the application page 705 may display an invitation card where the users are invited to enroll in the menstrual cycle tracking applications. The application page 705 may display a prompt to the user to verify whether the menstrual cycle may be tracked or dismiss the message if the menstrual cycle is not tracked.

In some cases, if the user does not have history data (e.g., temperature data for at least 60 calendar days), the system may utilize the calendar method until the system may identify a menstrual cycle phase and/or predict a future menstrual cycle phase. The system may receive an indication of whether the user selects to opt-in to tracking the menstrual cycle or opt-out to tracking the menstrual cycle.

The user may be presented with an application page 705 upon selecting "yes" to tracking the menstrual cycle. The application page 705 may display a prompt to the user to verify the main reason to track the cycle (e.g., period, ovulation, pregnancy, etc.). In such cases, the application page 705 may prompt the user to confirm the intent of tracking the menstrual cycle. For example, the system may receive, via the user device, a confirmation of the intended use of the menstrual tracking system.

In some cases, the user may be presented with an application page 705 upon confirming the intent. The application page 705 may display a prompt to the user to verify the average cycle length (e.g., duration between a first day of a first menstrual cycle and a first day of a second menstrual cycle). In some cases, the application page 705 may display a prompt to the user to indicate whether the user experiences irregular cycles in which an average cycle length may not be determined. For example, the system may receive, via the user device, a confirmation of the average cycle length.

The user may be presented with an application page 705 upon inputting the average cycle length or irregular cycle. The application page 705 may display a prompt to the user to verify the last cycle start date (e.g., a first day of the most recent menstrual cycle). The application page 705 may display a prompt to the user to indicate whether the user may be unable to identify the last cycle start date. For example, the system may receive, via the user device, a confirmation of the last cycle start date.

In some cases, the user may be presented with an application page 705 upon confirming the last cycle start date. The application page may display a prompt to the user to verify whether the user uses hormonal contraceptives in use. For example, the system may receive, via the user device, a confirmation of whether hormonal contraceptives are in use. Upon confirming that hormonal contraceptives are not in use, the user may be presented with a GUI 700 that may be further shown and described with reference to application page 705-*a* and/or application page 705-*b*.

The server of system may cause the GUI 700 of the user device (e.g., mobile device) to display an indication of the identified menstrual cycle phase (e.g., via application page 705-*a* or 705-*b*). In such cases, the system may output the identified menstrual cycle phases on the GUI 700 of the user device to indicate that the user is experiencing a first day of menstruation, ovulation, and the like or previously experienced a first day of menstruation, ovulation, and the like.

Continuing with the example above, upon identifying one or more menstrual cycle phases, the user may be presented with the application page 705-*a* upon opening the wearable application. As shown in FIG. 7, the application page 705-*a* may display an indication that one or more menstrual cycle phases were identified via message 720. In such cases, the application page 705-*a* may include the message 720 on the home page. In cases where a user's menstrual cycle phases may be identified, as described herein, the server may transmit a message 720 to the user, where the message 720 is associated with the identified menstrual cycle phase for the user.

For example, the user may receive message 720, which may indicate a time of day during which the identified one or more menstrual cycle phases occurred, a duration between a future menstrual cycle phase and a previous menstrual cycle phase, a time interval during which a future menstrual cycle phase is predicted to occur, and the like. For example, the message 720 may indicate that a period is likely starting tomorrow, in 5-7 days, or indicate a date of the predicted period onset day (e.g., predicted period start date is August 28th) or a range of dates of the predicted period onset day (e.g., predicted period start date April 27-29th). In such cases, the range may include the day of the predicted period onset day and the day before and after the predicted onset day. In some examples, the message 720 may indicate that the user is currently ovulating or predicted to ovulation in a given range of dates. The messages 720 may be configurable/customizable, such that the user may receive different messages 720 based on the identified menstrual cycle phases, as described previously herein.

As shown in FIG. 7, the application page 705-a may display an indication of the identified menstrual cycle phases via alert 710. The user may receive alert 710, which may prompt the user to verify whether the identified menstrual cycle phases have occurred or dismiss the alert 710 if the identified menstrual cycle phases have not occurred. In such cases, the application page 705-a may prompt the user to confirm or dismiss the identified menstrual cycle phases (e.g., confirm/deny whether the system correctly identified the menstrual cycle phases). For example, the system may receive, via the user device and in response to identifying the menstrual cycle phases, a confirmation of the identified menstrual cycle phases. Additionally, in some implementations, the application page 705-a may display one or more scores (e.g., Sleep Score, Readiness Score, etc.) for the user for the respective day.

The application pages 705 may display a period card or ovulation card such as a "identified menstrual cycle phases confirmation card" which indicates that the identified menstrual cycle phases have been recorded. In some implementations, upon confirming that the identified menstrual cycle phases are valid, the menstrual cycle phase may be recorded/logged in an activity log for the user for the respective calendar day. Moreover, in some cases, the menstrual cycle phase may be used to update (e.g., modify) one or more scores associated with the user (e.g., Sleep Score, Readiness Score, etc.). That is, data associated with the identified menstrual cycle phases may be used to update the scores for the user for the following calendar day after which the menstrual cycle phase was confirmed.

In some cases, the Readiness Score may be updated based on the identified menstrual cycle phases. For example, an elevated body temperature prior to the identified menstrual cycle phases may cause the system to alert the user, via alert 710, about their body signals (e.g., elevated body temperature). In such cases, the Readiness Score may indicate to the user to "pay attention" based on the phase of the menstrual cycle (e.g., that the identified menstrual cycle phases are approaching). If the Readiness Score changes for the user, the system may implement a cycle recovery mode for users whose cycle symptoms may be severe and may benefit from adjusted activity and readiness guidance for a couple of days. In other examples, the Readiness Score may be updated based on the Sleep Score and elevated body temperatures. However, the system may determine that the user is experiencing the menstrual period and may adjust (e.g., increase) the Readiness Score and/or Sleep Score to offset the effects of the menstrual cycle.

In some cases, the messages 720 displayed to the user via the GUI 700 of the user device may indicate how the identified menstrual cycle phases affected the overall scores (e.g., overall Readiness Score) and/or the individual contributing factors. For example, a message may indicate "It looks like your body is under strain right now, but if you're feeling ok, doing a light or medium intensity exercise can help your body battle the symptoms" or "From your recovery metrics it looks like your body is still doing ok, so some light activity can help relieve the symptoms. Hope you'll feel better tomorrow!" In cases where the timing/duration of the identified menstrual cycle phases was not optimal, the messages 720 may provide suggestions for the user in order to improve their general health. For example, the message may indicate "If you feel really low on energy, why not switch to rest mode for today," or "Since you have cramps and a headache, devote today for rest." In such cases, the messages 720 displayed to the user may provide targeted insights to help the user adjust their lifestyle during a portion of the menstrual cycle (e.g., during menstruation, ovulation, or the uterine cycle).

For users whose body signals (e.g., body temperature, heart rate, HRV, and the like) may react to the phase of the menstrual cycle, the system may display low activity goals around the identified menstrual cycle phase. In such cases, accurately identifying menstrual cycle phases may increase the accuracy and efficiency of the Readiness Score and Activity Scores. In some cases, the system may provide training insights and recommendations for athletes and other users during a portion of their menstrual cycle (i.e., suggesting increased intensity workouts during the first half of their cycle and lower intensity workouts during the second half of their cycle).

In cases where the user dismisses the prompt (e.g., alert 710) on application page 705-a, the prompt may disappear, and the user may input an indication of a first day of the period, ovulation, and the like via user input 725 at a later time. For example, if the user's period occurs after the predicted period onset day, the system may display the message 720 every day during the predicted range of days. If the user's period does not occur during the range of predicted days, then the system may prompt the user to input the period start date, via user input 725, when the period occurs. In some cases, the system may display via message 720 a prompt asking the user if the user is pregnant or suggests switching to an alternative mode (e.g., pregnancy mode) or deactivating period mode or ovulation mode.

In other examples, if the user's period starts early (i.e., the first day of the period occurs before the predicted period onset), the user may submit an indication of the first day of the period onset (e.g., a menstrual cycle phase) via user input 725. In some cases, identifying the one or more menstrual cycle phases may be based on receiving the indication. For example, the server of system may receive information, via user input 725, associated with the menstrual cycle phase.

The application page 705-a may indicate one or more parameters of the period, including a temperature, heart rate, HRV, and the like experienced by the user during the menstrual cycle via the time series 715. The time series 715 may be an example of the time series 350, as described with reference to FIG. 3.

In some cases, the user may log symptoms via user input 725. For example, the system may receive user input (e.g., tags) to log symptoms associated with the period, ovulation, or the like (e.g., flow, cramps, headaches, hot flashes, migraine, pain, pregnancy, etc.). The system may recommend tags to the user based on user history and the identified menstrual cycle phases. In some cases, the system may cause the GUI 700 of the user device to display menstrual cycle symptom tags based on a correlation between prior user symptom tags and a timing of the one or more menstrual cycle phases.

Application page 705-*a* may also include message 720 that includes insights, recommendations, and the like associated with the period. The server of system may cause the GUI 700 of the user device to display a message 720 associated with the identified menstrual cycle phase. The user device may display recommendations and/or information associated with the period via message 720. As noted previously herein, an accurately identified menstrual cycle phases may be beneficial to a user's overall health. In some implementations, the user device and/or servers may generate alerts 710 associated with the menstrual cycle phase which may be displayed to the user via the GUI 700 (e.g., application page 705-*a*). In particular, messages 720 generated and displayed to the user via the GUI 700 may be associated with one or more characteristics (e.g., time of day, duration) of the identified menstrual cycle phases.

For example, the message 720 may include a time of day during which the identified one or more menstrual cycle phases occurred, a duration between a future menstrual cycle phase and a previous menstrual cycle phase, a time interval during which a future menstrual cycle phase is predicted to occur, a request to input symptoms associated with the identified one or more menstrual cycle phases, or a combination thereof. In some cases, the message 720 may display a recommendation of how the user may adjust their lifestyle in the days leading up to the identified menstrual cycle phases, on the day of the identified menstrual cycle phases, and/or in the days after the identified menstrual cycle phases. In some examples, if the user tags "cramps" on cycle day 21 for the previous cycles, the system may display via message 720 a prompt that suggests logging "cramps" via user input 725 on or near cycle day 21. In other examples, the system may recommend a time (e.g., calendar day) for the user to be active or estimate a restorative time following the identified menstrual cycle phases.

In some implementations, the system may provide additional insight regarding the user's identified menstrual cycle phases. For example, the application pages 705 may indicate one or more physiological parameters (e.g., contributing factors) which resulted in the user's identified menstrual cycle phases, such as increased temperature, and the like. In other words, the system may be configured to provide some information or other insights regarding the identified menstrual cycle phases. Personalized insights may indicate aspects of collected physiological data (e.g., contributing factors within the physiological data) which were used to generate the identified menstrual cycle phases.

In some implementations, the system may be configured to receive user inputs regarding identified/predicted menstrual cycle phase in order to train classifiers (e.g., supervised learning for a machine learning classifier) and improve period determination and/or prediction techniques. For example, the user device may display a predicted period onset day or range of days indicating a relative likelihood that the user will experience a first day of a period. Subsequently, the user may input one or more user inputs, such as an onset of symptoms, a confirmation of the period onset, and the like. These user inputs 725 may then be input into the classifier to train the classifier. In other words, the user inputs 725 may be used to validate, or confirm, the menstrual cycle phase.

In some cases, the system may be configured to identify the menstrual cycle phases based on the user inputs such as a phase of the menstrual cycle and symptoms associated with the phase. For example, the system may receive user input 725 of ovulation and symptoms associated with ovulation. The system may identify a pattern of user inputs indicating ovulation that occur ten days prior to the identified period onset. In such cases, the system may adjust the identified period onset to be 10 days from the received user input of ovulation.

Upon identifying the one or more menstrual cycle phases on application page 705-*a*, the GUI 700 may display a portion of application page 705-*b*. In some cases, application page 705-*b* may include a calendar view 730 that may indicate a current date 735 that the user is viewing application page 705-*b* and a date range including the day 740 when the menstrual cycle phase (e.g., period onset day, ovulation) is predicted. For example, the date range may encircle the calendar days using a dashed line configuration, the current date 735 may encircle the calendar day, and the day 740 when the menstrual cycle phase (e.g., period onset, ovulation) is predicted may be encircled. The calendar view 730 may also include a message including the current calendar day and indication of the day of the user's cycle (e.g., 28th day of cycle).

In some cases, the system may retroactively label historical menstrual cycle phases. The calendar view 730 may include tagged events. For example, the tagged events may be indicated as open/filled circles under the calendar dates. Some tagged events (e.g., filled circles) may indicate detected cycle events, such as period onset events, ovulation, and the like.

In some implementations, the system may include one or more computing devices for different users. For example, the system may include computing devices for a primary user and a second user associated with the primary user (e.g., partner). The computing devices may measure physiological parameters of the different users, provide GUIs 700 for the different users, and receive user input 725 from the different users. In some implementations, the different computing devices may acquire physiological information and provide output related to a woman's health, such as menstruation, ovarian cycles, illness, fertility, and/or pregnancy. In some implementations, the different computing devices may acquire physiological information related to the second user, such as male illness and fertility.

In some implementations, the system may provide GUIs 700 that inform the second user of relevant information. For example, the second user may share their information with one another via one or more computing devices, such as via a server device, mobile device, or other device. In some implementations, the second user may share one or more of their accounts (e.g., usernames, login information, etc.) and/or associated data with one another. By sharing information between users, the system may assist second users in making health decisions related to fertility and pregnancy. In some implementations, the users may be prompted (e.g., in a GUI 700) to share specific information. For example, the user may use a GUI 700 to opt into sharing her ovulation information with the second user. In such cases, the user and the second user may receive notifications of an ovulation window on their respective computing devices. In other examples, a second user may make their information (e.g., illness, fertility data, etc.) available to the user via a notification or other sharing arrangement.

In some cases, the system may use sleep pattern data to generate user insights (e.g., personal/aggregate insights) via GUI 700. For example, the system may indicate that a user's deep sleep was low last night, but that it may be normal for this point in their menstrual cycle. As another example, the system may provide recommendations, such as recommendations to focus on getting to bed early, minimizing late night caffeine, meals, and/or alcohol in order to get more deep sleep.

In some implementations, the system may provide insights, via message 720, based on personal/aggregate user patterns for traveling, fasting, and other user activities (e.g., based on acquired tag data). Example insights may include, but are not limited to, insights into one or more cycle change characteristics, such as cycle length. With respect to travel, the system may indicate to the user that their cycle length may be modified based on their recent travel. In some cases, the system may request that the user provide tags indicating whether they are fasting or traveling.

The system may provide a variety of personalized insights. For example, the system may provide a user a message 720 that informs the user that they appear to get more deep sleep or tag headaches more frequently at certain times in their cycle. The insights may be derived from the statistical likelihood that a given tag is associated with a given point in the temperature-defined cycle. In some implementations, the system may send a user a personalized insight via message 720 when the system identifies a statistically definable change in the pattern of their cycle. In some implementations, the system may make recommendations for athletes or special forces, for example, about times in their cycle when they might consider intensifying their training versus building in more recovery time.

In some cases, a change in cycle length may be determined for fasting users. For example, some users may engage in time restricted feeding as a form of fasting, which may include limiting food consumption to a time window (e.g., 6 or 8 hours) during the day and extending the nighttime fasting period. The intermittent fasting may reduce the amount of time during the day that a person's blood glucose and insulin are in a postprandial state (e.g., elevated state) which may reduce oxidative stress and insulin sensitivity. In some cases, moderate fasting followed by sufficient recovery may have effects on the length of a menstrual cycle (e.g., lengthening the cycle). In some cases, the effects may be observed within a 1-3 month window.

For example, menstrual cycles following fasting may be longer (e.g., 1.4 days longer on average after tagging fasting). The increase may be most prominent 1-2 cycles or 30-60 days following fasting. The cycle changes may be associated with changes in metabolism or oxidative stress that follows moderate fasting with appropriate recovery (e.g., to avoid the body going into starvation mode). To control for other potentially confounding effects of time, the data associated with a late meal tag may be contrasted with the fasting tag. The system may detect/predict menstrual cycle phases at the level of subgroups of similar users or individual users and to display personalized trends and insights to users. For example, the system may identify that a user had indicated an interest in fertility and had recently inputted a fasting tag. In such cases, the system may send the user an insight with a link to further educational materials or a blog discussing links between intermittent fasting, diet/nutrition, fertility, timing ovulation, and the like.

In some cases, physiologically-based cycle estimation, as implemented by the system, may be more useful than a calendar-based algorithm that assumes a user's cycles are typically the same length every month. The advantages of a physiologically-based cycle-estimation algorithm over a calendar-based algorithm may be greater for users who may have less regular cycles due to birth control, older age, medical conditions, or other recent events. A more flexible physiologically-based cycle-phase estimation algorithm may provide unique value capture, especially for users who are experiencing changes that dramatically affect their cycling, such as the start or end of a pregnancy, recovering from a miscarriage, the end (or significant reductions) in breast-feeding, changes in birth control, a major sickness, or the start of hormonal/perimenopausal therapeutics.

Figure 8:
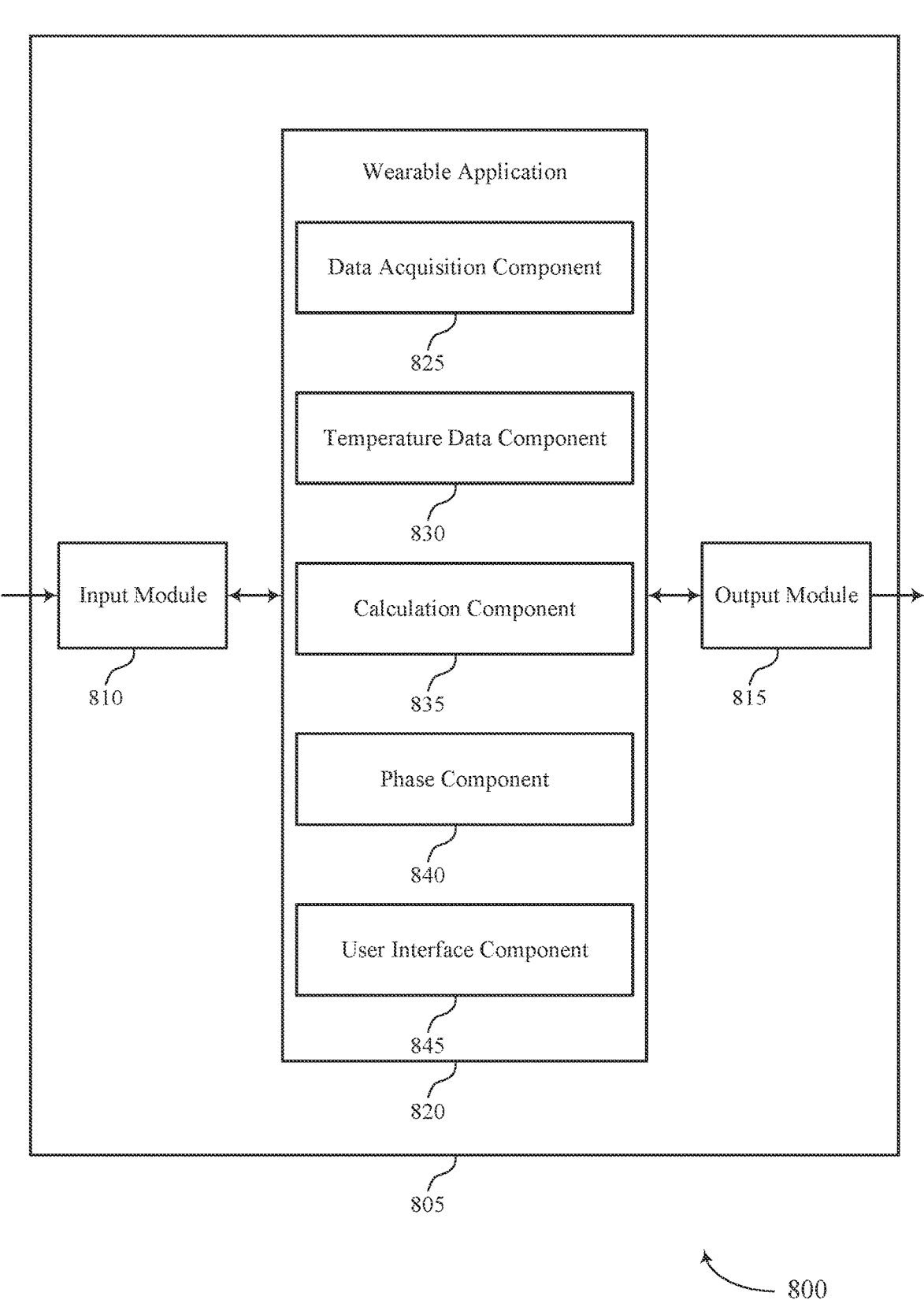
FIG. 8 shows a block diagram of an apparatus that supports menstrual cycle tracking in accordance with aspects of the present disclosure.

FIG. 8 shows a block diagram 800 of a device 805 that supports menstrual cycle tracking in accordance with aspects of the present disclosure. The device 805 may include an input module 810, an output module 815, and a wearable application 820. The device 805 may also include a processor. Each of these components may be in communication with one another (e.g., via one or more buses).

The input module 810 may provide a means for receiving information such as packets, user data, control information, or any combination thereof associated with various information channels (e.g., control channels, data channels, information channels related to illness detection techniques). Information may be passed on to other components of the device 805. The input module 810 may utilize a single antenna or a set of multiple antennas.

The output module 815 may provide a means for transmitting signals generated by other components of the device 805. For example, the output module 815 may transmit information such as packets, user data, control information, or any combination thereof associated with various information channels (e.g., control channels, data channels, information channels related to illness detection techniques). In some examples, the output module 815 may be co-located with the input module 810 in a transceiver module. The output module 815 may utilize a single antenna or a set of multiple antennas.

For example, the wearable application 820 may include a data acquisition component 825, a temperature data component 830, a calculation component 835, a phase component 840, a user interface component 845, or any combination thereof. In some examples, the wearable application 820, or various components thereof, may be configured to perform various operations (e.g., receiving, monitoring, transmitting) using or otherwise in cooperation with the input module 810, the output module 815, or both. For example, the wearable application 820 may receive information from the input module 810, send information to the output module 815, or be integrated in combination with the input module 810, the output module 815, or both to receive information, transmit information, or perform various other operations as described herein.

The wearable application 820 may support identifying a menstrual cycle phase at a user device in accordance with examples as disclosed herein. The data acquisition component 825 may be configured as or otherwise support a means for receiving physiological data associated with a user from a wearable device, the physiological data comprising at least temperature data. The temperature data component 830 may be configured as or otherwise support a means for determining a time series of a plurality of temperature values taken over a plurality of days based at least in part on the received temperature data, wherein the time series comprises a plurality of menstrual cycles for the user. The calculation component 835 may be configured as or otherwise support a means for identifying one or more morphological features of the time series of the plurality of temperature values based at least in part on determining the time series. The phase component 840 may be configured as or otherwise support a means for identifying one or more menstrual cycle phases in the time series based at least in part on identifying the one or more morphological features of the time series, wherein each menstrual cycle phase of the one or more menstrual cycle phases is associated with a morphological feature in the time series. The user interface component 845 may be configured as or otherwise support a means for causing a graphical user interface of the user device to display the identified one or more menstrual cycle phases.

Figure 9:
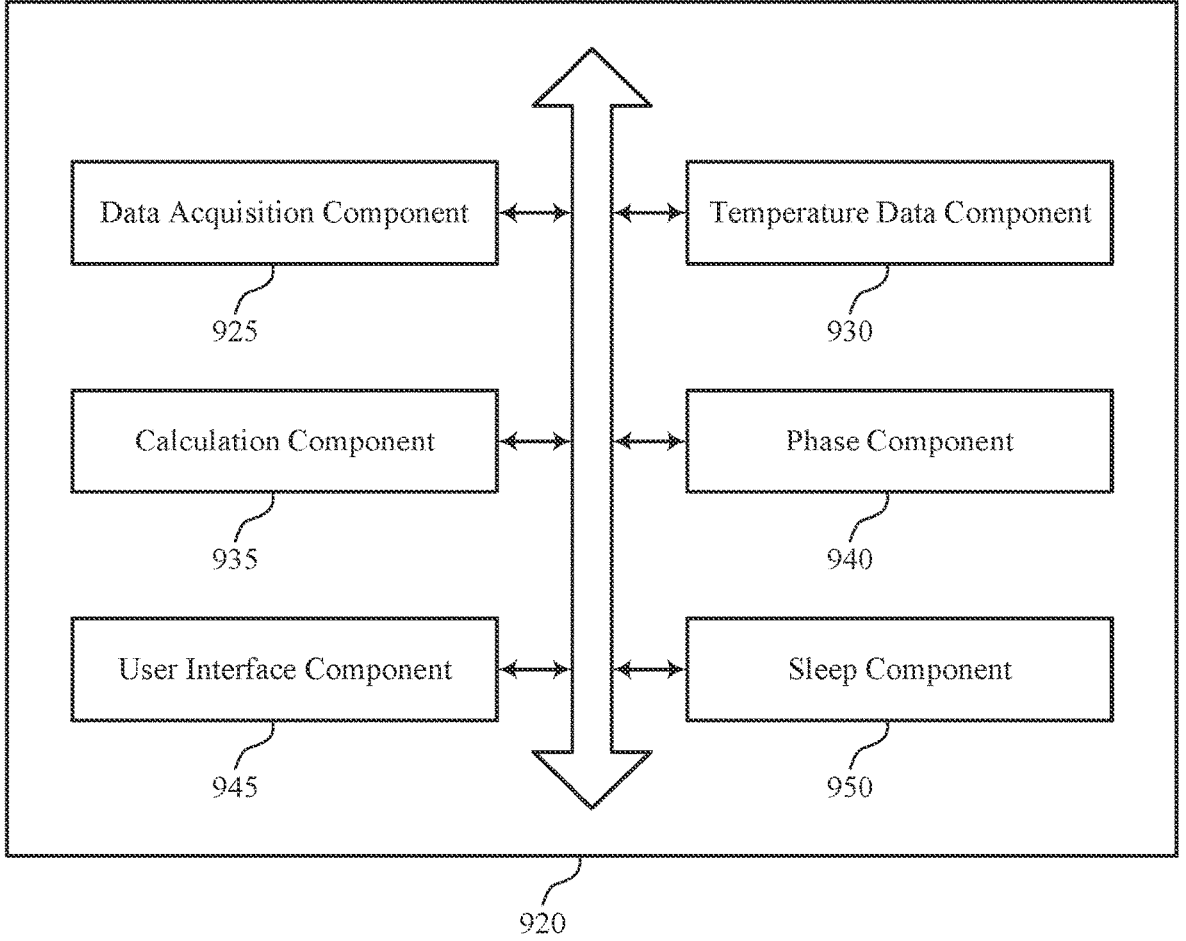
FIG. 9 shows a block diagram of a wearable application that supports menstrual cycle tracking in accordance with aspects of the present disclosure.

FIG. 9 shows a block diagram 900 of a wearable application 920 that supports menstrual cycle tracking in accordance with aspects of the present disclosure. The wearable application 920 may be an example of aspects of a wearable application or a wearable application 820, or both, as described herein. The wearable application 920, or various components thereof, may be an example of means for performing various aspects of menstrual cycle tracking as described herein. For example, the wearable application 920 may include a data acquisition component 925, a temperature data component 930, a calculation component 935, a phase component 940, a user interface component 945, a sleep component 950, or any combination thereof. Each of these components may communicate, directly or indirectly, with one another (e.g., via one or more buses).

The wearable application 920 may support identifying a menstrual cycle phase at a user device in accordance with examples as disclosed herein. The data acquisition component 925 may be configured as or otherwise support a means for receiving physiological data associated with a user from a wearable device, the physiological data comprising at least temperature data. The temperature data component 930 may be configured as or otherwise support a means for determining a time series of a plurality of temperature values taken over a plurality of days based at least in part on the received temperature data, wherein the time series comprises a plurality of menstrual cycles for the user. The calculation component 935 may be configured as or otherwise support a means for identifying one or more morphological features of the time series of the plurality of temperature values based at least in part on determining the time series. The phase component 940 may be configured as or otherwise support a means for identifying one or more menstrual cycle phases in the time series based at least in part on identifying the one or more morphological features of the time series, wherein each menstrual cycle phase of the one or more menstrual cycle phases is associated with a morphological feature in the time series. The user interface component 945 may be configured as or otherwise support a means for causing a graphical user interface of the user device to display the identified one or more menstrual cycle phases.

In some examples, the calculation component 935 may be configured as or otherwise support a means for computing a derivative of the time series of the plurality of temperatures. In some examples, the calculation component 935 may be configured as or otherwise support a means for identifying one or more local maximum or one or more local minimum of the derivative of the time series, wherein each menstrual cycle phase of the one or more of menstrual cycle phases is associated with the one or more local maximum or the one or more local minimum of the derivative of the time series.

In some examples, the calculation component 935 may be configured as or otherwise support a means for inverting the derivative of the time series of the plurality of temperatures based at least in part on computing the derivative of the time series. In some examples, the calculation component 935 may be configured as or otherwise support a means for identifying one or more local maximum of the inverted derivative of the time series, wherein each menstrual cycle phase of the one or more menstrual cycle phases is associated with the one or more local maximum of the inverted derivative of the time series.

In some examples, the sleep component 950 may be configured as or otherwise support a means for identifying a sleep period of the user based at least in part on determining the time series of the plurality of temperature values. In some examples, the sleep component 950 may be configured as or otherwise support a means for selecting a portion of the sleep period of the user, wherein identifying the one or more morphological features of the time series of the plurality of temperature values is based at least in part on selecting the portion of the sleep period.

In some examples, the temperature data component 930 may be configured as or otherwise support a means for determining each temperature value of the plurality of temperature values based at least in part on receiving the temperature data, wherein the temperature data comprises continuous nighttime temperature data.

In some examples, the sleep component 950 may be configured as or otherwise support a means for selecting a portion of a sleep period of the user based at least in part on historical temperature patterns for the user, wherein determining each temperature value of the plurality of temperature values is based at least in part on selecting the portion of the sleep period.

In some examples, the calculation component 935 may be configured as or otherwise support a means for identifying one or more maximum negative slopes of the time series of the plurality of temperature values based at least in part on identifying the one or more morphological features, wherein each menstrual cycle phase of the one or more menstrual cycle phases is associated with a maximum negative slope.

In some examples, the physiological data further comprises heart rate data, and the data acquisition component 925 may be configured as or otherwise support a means for determining that the received heart rate data satisfies a threshold for at least a portion of the plurality of days, wherein identifying the one or more menstrual cycle phases in the time series is based at least in part on determining that the received heart rate data satisfies the threshold.

In some examples, the physiological data further comprises respiratory rate data, and the data acquisition component 925 may be configured as or otherwise support a means for determining that the received respiratory rate data satisfies a threshold for at least a portion of the plurality of days, wherein identifying the one or more menstrual cycle phases in the time series is based at least in part on determining that the received respiratory rate data satisfies the threshold.

In some examples, the temperature data component 930 may be configured as or otherwise support a means for determining each temperature value of the plurality of temperature values based at least in part on receiving the temperature data, wherein the temperature data comprises continuous daytime temperature data.

In some examples, the phase component 940 may be configured as or otherwise support a means for identifying additional menstrual cycle events based at least in part on determining the time series of the plurality of temperature values.

In some examples, the phase component 940 may be configured as or otherwise support a means for estimating a future menstrual cycle phase during which the user experiences a first day of a menstrual cycle based at least in part on at least the time series of the plurality of temperature values, the identified one or more menstrual cycle phases, or both.

In some examples, the calculation component 935 may be configured as or otherwise support a means for updating a readiness score associated with the user based at least in part on the future menstrual cycle phase.

In some examples, the user interface component 945 may be configured as or otherwise support a means for causing the graphical user interface of the user device to display menstrual cycle symptom tags based at least in part on a correlation between prior user symptom tags and a timing of the one or more menstrual cycle phases.

In some examples, the phase component 940 may be configured as or otherwise support a means for estimating a length of the user's current menstrual cycle based at least in part on a morphology of the time series of the plurality of temperature values after a previous menstrual cycle.

In some examples, the phase component 940 may be configured as or otherwise support a means for identifying ovarian cycle events during the plurality of days based at least in part on the time series of the plurality of temperature values, wherein the one or more menstrual cycle phases comprises the ovarian cycle events.

In some examples, the phase component 940 may be configured as or otherwise support a means for identifying ovarian cycle events during the plurality of days based at least in part on heart rate data, respiratory rate data, or both, wherein the one or more menstrual cycle phases comprises the ovarian cycle events.

In some examples, the data acquisition component 925 may be configured as or otherwise support a means for inputting the physiological data into a machine learning classifier, wherein identifying the one or more menstrual cycle phases is based at least in part on inputting the physiological data into the machine learning classifier.

In some examples, the phase component 940 may be configured as or otherwise support a means for receiving, via the user device and in response to identifying the one or more menstrual cycle phases, a confirmation of the identified one or more menstrual cycle phases.

In some examples, the phase component 940 may be configured as or otherwise support a means for receiving, via the user device, an indication of a menstrual cycle phase, one or more symptoms associated with the menstrual cycle phase, or both, wherein identifying the one or more menstrual cycle phases is based at least in part on receiving the indication of the menstrual cycle phase, the one or more symptoms associated with the menstrual cycle phase, or both.

In some examples, the user interface component 945 may be configured as or otherwise support a means for causing the graphical user interface of the user device to display a message associated with the identified one or more menstrual cycle phases.

In some examples, the message comprises a time of day during which the identified one or more menstrual cycle phases occurred, a duration between a future menstrual cycle phase and a previous menstrual cycle phase, a time interval during which a future menstrual cycle phase is predicted to occur, a request to input symptoms associated with the identified one or more menstrual cycle phases, a medical condition associated with the identified one or more menstrual cycle phases, educational content associated with the identified one or more menstrual cycle phases, or a combination thereof.

In some examples, the wearable device comprises a wearable ring device.

In some examples, the wearable device collects the physiological data from the user based on arterial blood flow.

Figure 10:
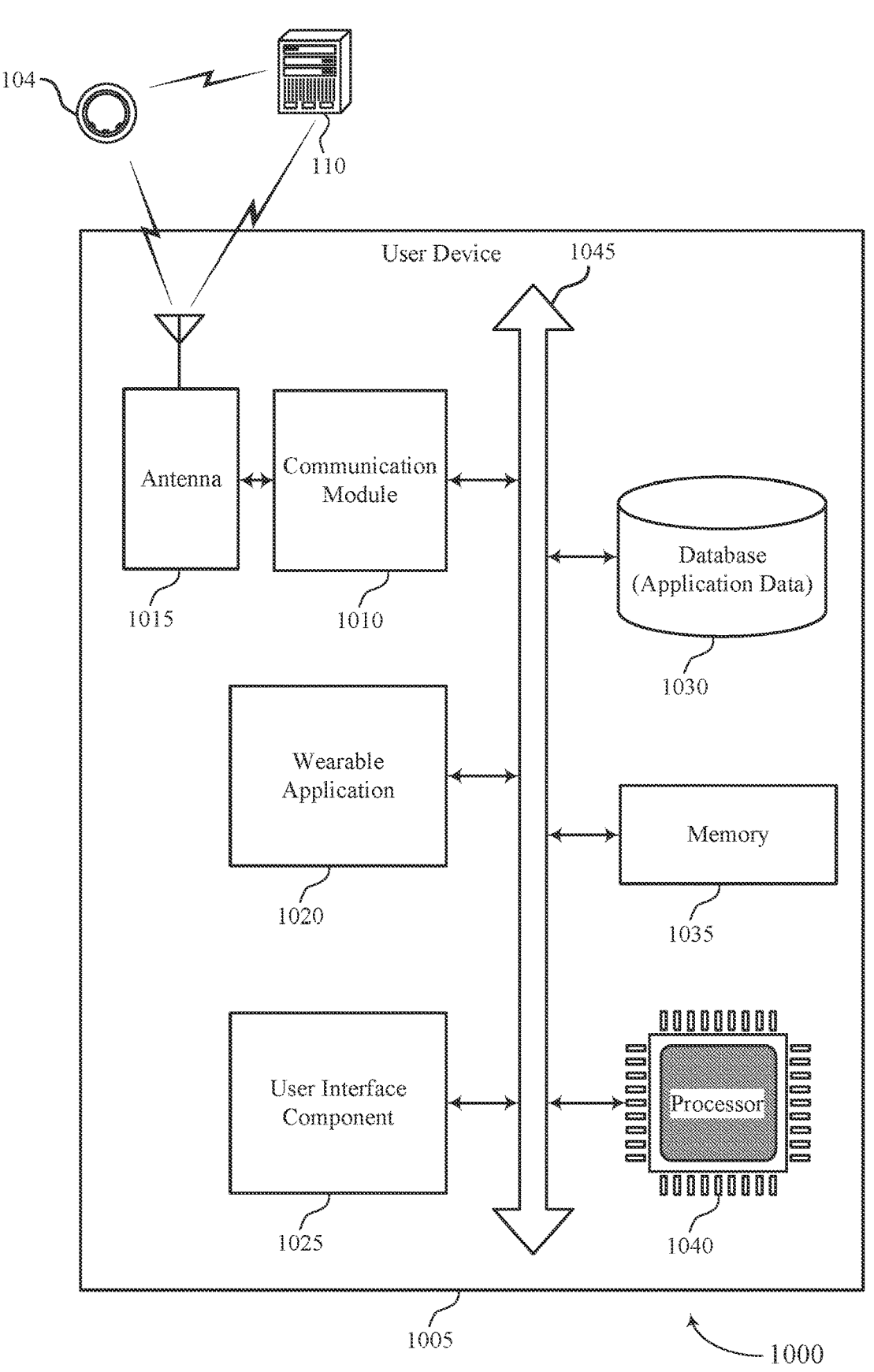
FIG. 10 shows a diagram of a system including a device that supports menstrual cycle tracking in accordance with aspects of the present disclosure.

FIG. 10 shows a diagram of a system 1000 including a device 1005 that supports menstrual cycle tracking in accordance with aspects of the present disclosure. The device 1005 may be an example of or include the components of a device 805 as described herein. The device 1005 may include an example of a user device 106, as described previously herein. The device 1005 may include components for bi-directional communications including components for transmitting and receiving communications with a wearable device 104 and a server 110, such as a wearable application 1020, a communication module 1010, an antenna 1015, a user interface component 1025, a database (application data) 1030, a memory 1035, and a processor 1040. These components may be in electronic communication or otherwise coupled (e.g., operatively, communicatively, functionally, electronically, electrically) via one or more buses (e.g., a bus 1045).

The communication module 1010 may manage input and output signals for the device 1005 via the antenna 1015. The communication module 1010 may include an example of the communication module 220-b of the user device 106 shown and described in FIG. 2. In this regard, the communication module 1010 may manage communications with the ring 104 and the server 110, as illustrated in FIG. 2. The communication module 1010 may also manage peripherals not integrated into the device 1005. In some cases, the communication module 1010 may represent a physical connection or port to an external peripheral. In some cases, the communication module 1010 may utilize an operating system such as iOS®, ANDROID®, MS-DOS®, MS-WINDOWS®, OS/2®, UNIX®, LINUX®, or another known operating system. In other cases, the communication module 1010 may represent or interact with a wearable device (e.g., ring 104), modem, a keyboard, a mouse, a touchscreen, or a similar device. In some cases, the communication module 1010 may be implemented as part of the processor 1040. In some examples, a user may interact with the device 1005 via the communication module 1010, user interface component 1025, or via hardware components controlled by the communication module 1010.

In some cases, the device 1005 may include a single antenna 1015. However, in some other cases, the device 1005 may have more than one antenna 1015, which may be capable of concurrently transmitting or receiving multiple wireless transmissions. The communication module 1010 may communicate bi-directionally, via the one or more antennas 1015, wired, or wireless links as described herein. For example, the communication module 1010 may represent a wireless transceiver and may communicate bi-directionally with another wireless transceiver. The communication module 1010 may also include a modem to modulate the packets, to provide the modulated packets to one or more antennas 1015 for transmission, and to demodulate packets received from the one or more antennas 1015.

The user interface component 1025 may manage data storage and processing in a database 1030. In some cases, a user may interact with the user interface component 1025. In other cases, the user interface component 1025 may operate automatically without user interaction. The database 1030 may be an example of a single database, a distributed database, multiple distributed databases, a data store, a data lake, or an emergency backup database.

The memory 1035 may include RAM and ROM. The memory 1035 may store computer-readable, computer-executable software including instructions that, when executed, cause the processor 1040 to perform various functions described herein. In some cases, the memory 1035 may contain, among other things, a BIOS which may control basic hardware or software operation such as the interaction with peripheral components or devices.

The processor 1040 may include an intelligent hardware device, (e.g., a general-purpose processor, a DSP, a CPU, a microcontroller, an ASIC, an FPGA, a programmable logic device, a discrete gate or transistor logic component, a discrete hardware component, or any combination thereof). In some cases, the processor 1040 may be configured to operate a memory array using a memory controller. In other cases, a memory controller may be integrated into the processor 1040. The processor 1040 may be configured to execute computer-readable instructions stored in a memory 1035 to perform various functions (e.g., functions or tasks supporting a method and system for sleep staging algorithms).

The wearable application 1020 may support identifying a menstrual cycle phase at a user device in accordance with examples as disclosed herein. For example, the wearable application 1020 may be configured as or otherwise support a means for receiving physiological data associated with a user from a wearable device, the physiological data comprising at least temperature data. The wearable application 1020 may be configured as or otherwise support a means for determining a time series of a plurality of temperature values taken over a plurality of days based at least in part on the received temperature data, wherein the time series comprises a plurality of menstrual cycles for the user. The wearable application 1020 may be configured as or otherwise support a means for identifying one or more morphological features of the time series of the plurality of temperature values based at least in part on determining the time series. The wearable application 1020 may be configured as or otherwise support a means for identifying one or more menstrual cycle phases in the time series based at least in part on identifying the one or more morphological features of the time series, wherein each menstrual cycle phase of the one or more menstrual cycle phases is associated with a morphological feature in the time series. The wearable application 1020 may be configured as or otherwise support a means for causing a graphical user interface of the user device to display the identified one or more menstrual cycle phases.

By including or configuring the wearable application 1020 in accordance with examples as described herein, the device 1005 may support techniques for improved communication reliability, reduced latency, improved user experience related to reduced processing, reduced power consumption, more efficient utilization of communication resources, improved coordination between devices, longer battery life, and improved utilization of processing capability.

The wearable application 1020 may include an application (e.g., "app"), program, software, or other component which is configured to facilitate communications with a ring 104, server 110, other user devices 106, and the like. For example, the wearable application 1020 may include an application executable on a user device 106 which is configured to receive data (e.g., physiological data) from a ring 104, perform processing operations on the received data, transmit and receive data with the servers 110, and cause presentation of data to a user 102.

FIG. 11 shows a flowchart illustrating a method 1100 that supports menstrual cycle tracking in accordance with aspects of the present disclosure. The operations of the method 1100 may be implemented by a user device or its components as described herein. For example, the operations of the method 1100 may be performed by a user device as described with reference to FIGS. 1 through 10. In some examples, a user device may execute a set of instructions to control the functional elements of the user device to perform the described functions. Additionally, or alternatively, the user device may perform aspects of the described functions using special-purpose hardware.

At 1105, the method may include receiving physiological data associated with a user from a wearable device, the physiological data comprising at least temperature data. The operations of 1105 may be performed in accordance with examples as disclosed herein. In some examples, aspects of the operations of 1105 may be performed by a data acquisition component 925 as described with reference to FIG. 9.

At 1110, the method may include determining a time series of a plurality of temperature values taken over a plurality of days based at least in part on the received temperature data, wherein the time series comprises a plurality of menstrual cycles for the user. The operations of 1110 may be performed in accordance with examples as disclosed herein. In some examples, aspects of the operations of 1110 may be performed by a temperature data component 930 as described with reference to FIG. 9.

At 1115, the method may include identifying one or more morphological features of the time series of the plurality of temperature values based at least in part on determining the time series. The operations of 1115 may be performed in accordance with examples as disclosed herein. In some examples, aspects of the operations of 1115 may be performed by a calculation component 935 as described with reference to FIG. 9.

At 1120, the method may include identifying one or more menstrual cycle phases in the time series based at least in part on identifying the one or more morphological features of the time series, wherein each menstrual cycle phase of the one or more menstrual cycle phases is associated with a morphological feature in the time series. The operations of 1120 may be performed in accordance with examples as disclosed herein. In some examples, aspects of the operations of 1120 may be performed by a phase component 940 as described with reference to FIG. 9.

At 1125, the method may include causing a graphical user interface of the user device to display the identified one or more menstrual cycle phases. The operations of 1125 may be performed in accordance with examples as disclosed herein. In some examples, aspects of the operations of 1125 may be performed by a user interface component 945 as described with reference to FIG. 9.

FIG. 12 shows a flowchart illustrating a method 1200 that supports menstrual cycle tracking in accordance with aspects of the present disclosure. The operations of the method 1200 may be implemented by a user device or its components as described herein. For example, the operations of the method 1200 may be performed by a user device as described with reference to FIGS. 1 through 10. In some examples, a user device may execute a set of instructions to control the functional elements of the user device to perform the described functions. Additionally, or alternatively, the user device may perform aspects of the described functions using special-purpose hardware.

At 1205, the method may include receiving physiological data associated with a user from a wearable device, the physiological data comprising at least temperature data. The operations of 1205 may be performed in accordance with examples as disclosed herein. In some examples, aspects of the operations of 1205 may be performed by a data acquisition component 925 as described with reference to FIG. 9.

At 1210, the method may include determining a time series of a plurality of temperature values taken over a plurality of days based at least in part on the received temperature data, wherein the time series comprises a plurality of menstrual cycles for the user. The operations of 1210 may be performed in accordance with examples as disclosed herein. In some examples, aspects of the operations of 1210 may be performed by a temperature data component 930 as described with reference to FIG. 9.

At 1215, the method may include computing a derivative of the time series of the plurality of temperatures. The operations of 1215 may be performed in accordance with examples as disclosed herein. In some examples, aspects of the operations of 1215 may be performed by a calculation component 935 as described with reference to FIG. 9.

At 1220, the method may include identifying one or more local maximum or one or more local minimum of the derivative of the time series, wherein each menstrual cycle phase of the one or more of menstrual cycle phases is associated with the one or more local maximum or the one or more local minimum of the derivative of the time series. The operations of 1220 may be performed in accordance with examples as disclosed herein. In some examples, aspects of the operations of 1220 may be performed by a calculation component 935 as described with reference to FIG. 9.

At 1225, the method may include identifying one or more morphological features of the time series of the plurality of temperature values based at least in part on determining the time series. The operations of 1225 may be performed in accordance with examples as disclosed herein. In some examples, aspects of the operations of 1225 may be performed by a calculation component 935 as described with reference to FIG. 9.

At 1230, the method may include identifying one or more menstrual cycle phases in the time series based at least in part on identifying the one or more morphological features of the time series, wherein each menstrual cycle phase of the one or more menstrual cycle phases is associated with a morphological feature in the time series. The operations of 1230 may be performed in accordance with examples as disclosed herein. In some examples, aspects of the operations of 1230 may be performed by a phase component 940 as described with reference to FIG. 9.

At 1235, the method may include causing a graphical user interface of the user device to display the identified one or more menstrual cycle phases. The operations of 1235 may be performed in accordance with examples as disclosed herein. In some examples, aspects of the operations of 1235 may be performed by a user interface component 945 as described with reference to FIG. 9.

FIG. 13 shows a flowchart illustrating a method 1300 that supports menstrual cycle tracking in accordance with aspects of the present disclosure. The operations of the method 1300 may be implemented by a user device or its components as described herein. For example, the operations of the method 1300 may be performed by a user device as described with reference to FIGS. 1 through 10. In some examples, a user device may execute a set of instructions to control the functional elements of the user device to perform the described functions. Additionally, or alternatively, the user device may perform aspects of the described functions using special-purpose hardware.

At 1305, the method may include receiving physiological data associated with a user from a wearable device, the physiological data comprising at least temperature data. The operations of 1305 may be performed in accordance with examples as disclosed herein. In some examples, aspects of the operations of 1305 may be performed by a data acquisition component 925 as described with reference to FIG. 9.

At 1310, the method may include determining a time series of a plurality of temperature values taken over a plurality of days based at least in part on the received temperature data, wherein the time series comprises a plurality of menstrual cycles for the user. The operations of 1310 may be performed in accordance with examples as disclosed herein. In some examples, aspects of the operations of 1310 may be performed by a temperature data component 930 as described with reference to FIG. 9.

At 1315, the method may include identifying a sleep period of the user based at least in part on determining the time series of the plurality of temperature values. The operations of 1315 may be performed in accordance with examples as disclosed herein. In some examples, aspects of the operations of 1315 may be performed by a sleep component 950 as described with reference to FIG. 9.

At 1320, the method may include selecting a portion of the sleep period of the user, wherein identifying the one or more morphological features of the time series of the plurality of temperature values is based at least in part on selecting the portion of the sleep period. The operations of 1320 may be performed in accordance with examples as disclosed herein. In some examples, aspects of the operations of 1320 may be performed by a sleep component 950 as described with reference to FIG. 9.

At 1325, the method may include identifying one or more morphological features of the time series of the plurality of temperature values based at least in part on determining the time series. The operations of 1325 may be performed in accordance with examples as disclosed herein. In some examples, aspects of the operations of 1325 may be performed by a calculation component 935 as described with reference to FIG. 9.

At 1330, the method may include identifying one or more menstrual cycle phases in the time series based at least in part on identifying the one or more morphological features of the time series, wherein each menstrual cycle phase of the one or more menstrual cycle phases is associated with a morphological feature in the time series. The operations of 1330 may be performed in accordance with examples as disclosed herein. In some examples, aspects of the operations of 1330 may be performed by a phase component 940 as described with reference to FIG. 9.

At 1335, the method may include causing a graphical user interface of the user device to display the identified one or more menstrual cycle phases. The operations of 1335 may be performed in accordance with examples as disclosed herein. In some examples, aspects of the operations of 1335 may be performed by a user interface component 945 as described with reference to FIG. 9.

It should be noted that the methods described above describe possible implementations, and that the operations and the steps may be rearranged or otherwise modified and that other implementations are possible. Furthermore, aspects from two or more of the methods may be combined.

A method for identifying a menstrual cycle phase at a user device is described. The method may include receiving physiological data associated with a user from a wearable device, the physiological data comprising at least temperature data, determining a time series of a plurality of temperature values taken over a plurality of days based at least in part on the received temperature data, wherein the time series comprises a plurality of menstrual cycles for the user, identifying one or more morphological features of the time series of the plurality of temperature values based at least in part on determining the time series, identifying one or more menstrual cycle phases in the time series based at least in part on identifying the one or more morphological features of the time series, wherein each menstrual cycle phase of the one or more menstrual cycle phases is associated with a morphological feature in the time series, and causing a graphical user interface of the user device to display the identified one or more menstrual cycle phases.

An apparatus for identifying a menstrual cycle phase at a user device is described. The apparatus may include a processor, memory coupled with the processor, and instructions stored in the memory. The instructions may be executable by the processor to cause the apparatus to receive physiological data associated with a user from a wearable device, the physiological data comprising at least temperature data, determine a time series of a plurality of temperature values taken over a plurality of days based at least in part on the received temperature data, wherein the time series comprises a plurality of menstrual cycles for the user, identify one or more morphological features of the time series of the plurality of temperature values based at least in part on determining the time series, identify one or more menstrual cycle phases in the time series based at least in part on identifying the one or more morphological features of the time series, wherein each menstrual cycle phase of the one or more menstrual cycle phases is associated with a morphological feature in the time series, and cause a graphical user interface of the user device to display the identified one or more menstrual cycle phases.

Another apparatus for identifying a menstrual cycle phase at a user device is described. The apparatus may include means for receiving physiological data associated with a user from a wearable device, the physiological data comprising at least temperature data, means for determining a time series of a plurality of temperature values taken over a plurality of days based at least in part on the received temperature data, wherein the time series comprises a plurality of menstrual cycles for the user, means for identifying one or more morphological features of the time series of the plurality of temperature values based at least in part on determining the time series, means for identifying one or more menstrual cycle phases in the time series based at least in part on identifying the one or more morphological features of the time series, wherein each menstrual cycle phase of the one or more menstrual cycle phases is associated with a morphological feature in the time series, and means for causing a graphical user interface of the user device to display the identified one or more menstrual cycle phases.

A non-transitory computer-readable medium storing code for identifying a menstrual cycle phase at a user device is described. The code may include instructions executable by a processor to receive physiological data associated with a user from a wearable device, the physiological data comprising at least temperature data, determine a time series of a plurality of temperature values taken over a plurality of days based at least in part on the received temperature data, wherein the time series comprises a plurality of menstrual cycles for the user, identify one or more morphological features of the time series of the plurality of temperature values based at least in part on determining the time series, identify one or more menstrual cycle phases in the time series based at least in part on identifying the one or more morphological features of the time series, wherein each menstrual cycle phase of the one or more menstrual cycle phases is associated with a morphological feature in the time series, and cause a graphical user interface of the user device to display the identified one or more menstrual cycle phases.

Some examples of the method, apparatuses, and non-transitory computer-readable medium described herein may further include operations, features, means, or instructions for computing a derivative of the time series of the plurality of temperatures and identifying one or more local maximum or one or more local minimum of the derivative of the time series, wherein each menstrual cycle phase of the one or more of menstrual cycle phases may be associated with the one or more local maximum or the one or more local minimum of the derivative of the time series.

Some examples of the method, apparatuses, and non-transitory computer-readable medium described herein may further include operations, features, means, or instructions for inverting the derivative of the time series of the plurality of temperatures based at least in part on computing the derivative of the time series and identifying one or more local maximum of the inverted derivative of the time series, wherein each menstrual cycle phase of the one or more menstrual cycle phases may be associated with the one or more local maximum of the inverted derivative of the time series.

Some examples of the method, apparatuses, and non-transitory computer-readable medium described herein may further include operations, features, means, or instructions for identifying a sleep period of the user based at least in part on determining the time series of the plurality of temperature values and selecting a portion of the sleep period of the user, wherein identifying the one or more morphological features of the time series of the plurality of temperature values may be based at least in part on selecting the portion of the sleep period.

Some examples of the method, apparatuses, and non-transitory computer-readable medium described herein may further include operations, features, means, or instructions for determining each temperature value of the plurality of temperature values based at least in part on receiving the temperature data, wherein the temperature data comprises continuous nighttime temperature data.

Some examples of the method, apparatuses, and non-transitory computer-readable medium described herein may further include operations, features, means, or instructions for selecting a portion of a sleep period of the user based at least in part on historical temperature patterns for the user, wherein determining each temperature value of the plurality of temperature values may be based at least in part on selecting the portion of the sleep period.

Some examples of the method, apparatuses, and non-transitory computer-readable medium described herein may further include operations, features, means, or instructions for identifying one or more maximum negative slopes of the time series of the plurality of temperature values based at least in part on identifying the one or more morphological features, wherein each menstrual cycle phase of the one or more menstrual cycle phases may be associated with a maximum negative slope.

In some examples of the method, apparatuses, and non-transitory computer-readable medium described herein, the physiological data further comprises heart rate data and the method, apparatuses, and non-transitory computer-readable medium may include further operations, features, means, or instructions for determining that the received heart rate data satisfies a threshold for at least a portion of the plurality of days, wherein identifying the one or more menstrual cycle phases in the time series may be based at least in part on determining that the received heart rate data satisfies the threshold.

In some examples of the method, apparatuses, and non-transitory computer-readable medium described herein, the physiological data further comprises respiratory rate data and the method, apparatuses, and non-transitory computer-readable medium may include further operations, features, means, or instructions for determining that the received respiratory rate data satisfies a threshold for at least a portion of the plurality of days, wherein identifying the one or more menstrual cycle phases in the time series may be based at least in part on determining that the received respiratory rate data satisfies the threshold.

Some examples of the method, apparatuses, and non-transitory computer-readable medium described herein may further include operations, features, means, or instructions for determining each temperature value of the plurality of temperature values based at least in part on receiving the temperature data, wherein the temperature data comprises continuous daytime temperature data.

Some examples of the method, apparatuses, and non-transitory computer-readable medium described herein may further include operations, features, means, or instructions for identifying additional menstrual cycle events based at least in part on determining the time series of the plurality of temperature values.

Some examples of the method, apparatuses, and non-transitory computer-readable medium described herein may further include operations, features, means, or instructions for estimating a future menstrual cycle phase during which the user experiences a first day of a menstrual cycle based at least in part on at least the time series of the plurality of temperature values, the identified one or more menstrual cycle phases, or both.

Some examples of the method, apparatuses, and non-transitory computer-readable medium described herein may further include operations, features, means, or instructions for updating a readiness score associated with the user based at least in part on the future menstrual cycle phase.

Some examples of the method, apparatuses, and non-transitory computer-readable medium described herein may further include operations, features, means, or instructions for causing the graphical user interface of the user device to display menstrual cycle symptom tags based at least in part on a correlation between prior user symptom tags and a timing of the one or more menstrual cycle phases.

Some examples of the method, apparatuses, and non-transitory computer-readable medium described herein may further include operations, features, means, or instructions for estimating a length of the user's current menstrual cycle based at least in part on a morphology of the time series of the plurality of temperature values after a previous menstrual cycle.

Some examples of the method, apparatuses, and non-transitory computer-readable medium described herein may further include operations, features, means, or instructions for identifying ovarian cycle events during the plurality of days based at least in part on the time series of the plurality of temperature values, wherein the one or more menstrual cycle phases comprises the ovarian cycle events.

Some examples of the method, apparatuses, and non-transitory computer-readable medium described herein may further include operations, features, means, or instructions for identifying ovarian cycle events during the plurality of days based at least in part on heart rate data, respiratory rate data, or both, wherein the one or more menstrual cycle phases comprises the ovarian cycle events.

Some examples of the method, apparatuses, and non-transitory computer-readable medium described herein may further include operations, features, means, or instructions for inputting the physiological data into a machine learning classifier, wherein identifying the one or more menstrual cycle phases may be based at least in part on inputting the physiological data into the machine learning classifier.

Some examples of the method, apparatuses, and non-transitory computer-readable medium described herein may further include operations, features, means, or instructions for receiving, via the user device and in response to identifying the one or more menstrual cycle phases, a confirmation of the identified one or more menstrual cycle phases.

Some examples of the method, apparatuses, and non-transitory computer-readable medium described herein may further include operations, features, means, or instructions for receiving, via the user device, an indication of a menstrual cycle phase, one or more symptoms associated with the menstrual cycle phase, or both, wherein identifying the one or more menstrual cycle phases may be based at least in part on receiving the indication of the menstrual cycle phase, the one or more symptoms associated with the menstrual cycle phase, or both.

Some examples of the method, apparatuses, and non-transitory computer-readable medium described herein may further include operations, features, means, or instructions for causing the graphical user interface of the user device to display a message associated with the identified one or more menstrual cycle phases.

In some examples of the method, apparatuses, and non-transitory computer-readable medium described herein, the message comprises a time of day during which the identified one or more menstrual cycle phases occurred, a duration between a future menstrual cycle phase and a previous menstrual cycle phase, a time interval during which a future menstrual cycle phase may be predicted to occur, a request to input symptoms associated with the identified one or more menstrual cycle phases, a medical condition associated with the identified one or more menstrual cycle phases, educational content associated with the identified one or more menstrual cycle phases, or a combination thereof.

In some examples of the method, apparatuses, and non-transitory computer-readable medium described herein, the wearable device comprises a wearable ring device.

In some examples of the method, apparatuses, and non-transitory computer-readable medium described herein, the wearable device collects the physiological data from the user based on arterial blood flow.

The description set forth herein, in connection with the appended drawings, describes example configurations and does not represent all the examples that may be implemented or that are within the scope of the claims. The term "exemplary" used herein means "serving as an example, instance, or illustration," and not "preferred" or "advantageous over other examples." The detailed description includes specific details for the purpose of providing an understanding of the described techniques. These techniques, however, may be practiced without these specific details. In some instances, well-known structures and devices are shown in block diagram form in order to avoid obscuring the concepts of the described examples.

In the appended figures, similar components or features may have the same reference label. Further, various components of the same type may be distinguished by following the reference label by a dash and a second label that distinguishes among the similar components. If just the first reference label is used in the specification, the description is applicable to any one of the similar components having the same first reference label irrespective of the second reference label.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and modules described in connection with the disclosure herein may be implemented or performed with a general-purpose processor, a DSP, an ASIC, an FPGA or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices (e.g., a combination of a DSP and a microprocessor, multiple microprocessors, one or more microprocessors in conjunction with a DSP core, or any other such configuration).

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope of the disclosure and appended claims. For example, due to the nature of software, functions described above can be implemented using software executed by a processor, hardware, firmware, hardwiring, or combinations of any of these. Features implementing functions may also be physically located at various positions, including being distributed such that portions of functions are implemented at different physical locations. Also, as used herein, including in the claims, "or" as used in a list of items (for example, a list of items prefaced by a phrase such as "at least one of" or "one or more of") indicates an inclusive list such that, for example, a list of at least one of A, B, or C means A or B or C or AB or AC or BC or ABC (i.e., A and B and C). Also, as used herein, the phrase "based on" shall not be construed as a reference to a closed set of conditions. For example, an exemplary step that is described as "based on condition A" may be based on both a condition A and a condition B without departing from the scope of the present disclosure. In other words, as used herein, the phrase "based on" shall be construed in the same manner as the phrase "based at least in part on."

Computer-readable media includes both non-transitory computer storage media and communication media including any medium that facilitates transfer of a computer program from one place to another. A non-transitory storage medium may be any available medium that can be accessed by a general purpose or special purpose computer. By way of example, and not limitation, non-transitory computer-readable media can comprise RAM, ROM, electrically erasable programmable ROM (EEPROM), compact disk (CD) ROM or other optical disk storage, magnetic disk storage or other magnetic storage devices, or any other non-transitory medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, include CD, laser disc, optical disc, digital versatile disc (DVD), floppy disk and Blu-ray disc where disks usually reproduce data magnetically, while discs reproduce data optically with lasers. Combinations of the above are also included within the scope of computer-readable media.

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not limited to the examples and designs described herein, but is to be accorded the broadest scope consistent with the principles and novel features disclosed herein.

What is claimed is:

1. A method for identifying a menstrual cycle phase at a user device, comprising:

measuring, using a wearable ring device configured to be worn on a finger of a user, physiological data comprising at least temperature data, wherein the wearable ring device comprises:

a ring-shaped housing;

one or more temperature sensors arranged within the ring-shaped housing, wherein the temperature data measured from the finger of the user captures a higher degree of temperature fluctuations as compared to core temperature measurements;

one or more processors disposed at least partially within the ring-shaped housing, the one or more processors electrically coupled with the one or more temperature sensors; and a communication module electrically coupled with the one or more processors, the communication module configured to transmit the physiological data generated by the one or more processors;

determining, via the one or more processors, a time series of a plurality of temperature values taken over a plurality of days based at least in part on the temperature data, wherein the time series comprises a plurality of menstrual cycles for the user;

computing, via the one or more processors, a derivative of the time series of the plurality of temperature values;

inverting, via the one or more processors, the derivative of the time series of the plurality of temperature values based at least in part on computing the derivative of the time series;

identifying, via the one or more processors, one or more morphological features of the inverted derivative identifying, via the one or more processors, one or more menstrual cycle phases in the time series based at least in part on identifying the one or more morphological features of the inverted derivative of the time series and the temperature data continuously measured being indicative of the temperature fluctuations, wherein each menstrual cycle phase of the one or more menstrual cycle phases is associated with a morphological feature in the inverted derivative of the time series; and transmitting, via the communication module, one or more signals to a user device to cause a graphical user interface of the user device to display the one or more menstrual cycle phases.

2. The method of claim 1, further comprising:

identifying one or more local maximum or one or more local minimum of the derivative of the time series, wherein each menstrual cycle phase of the one or more of menstrual cycle phases is associated with the one or more local maximum or the one or more local minimum of the derivative of the time series.

3. The method of claim 2, further comprising:

identifying one or more local maximum of the inverted derivative of the time series, wherein each menstrual cycle phase of the one or more menstrual cycle phases is associated with the one or more local maximum of the inverted derivative of the time series.

4. The method of claim 1, further comprising:

identifying a sleep period of the user based at least in part on determining the time series of the plurality of temperature values; and selecting a portion of the sleep period of the user, wherein identifying the one or more morphological features of the inverted derivative of the time series of the plurality of temperature values is based at least in part on selecting the portion of the sleep period.

5. The method of claim 1, further comprising:

determining each temperature value of the plurality of temperature values based at least in part on receiving the temperature data, wherein the temperature data comprises continuous nighttime temperature data.

6. The method of claim 5, further comprising:

selecting a portion of a sleep period of the user based at least in part on historical temperature patterns for the user, wherein determining each temperature value of the plurality of temperature values is based at least in part on selecting the portion of the sleep period.

7. The method of claim 1, further comprising:

identifying one or more maximum negative slopes of the time series of the plurality of temperature values based at least in part on identifying the one or more morphological features, wherein each menstrual cycle phase of the one or more menstrual cycle phases is associated with a maximum negative slope.

8. The method of claim 1, wherein the physiological data further comprises heart rate data, the method further comprising:

determining that the heart rate data satisfies a threshold for at least a portion of the plurality of days, wherein identifying the one or more menstrual cycle phases in the inverted derivative of the time series is based at least in part on determining that the heart rate data satisfies the threshold.

9. The method of claim 1, wherein the physiological data further comprises respiratory rate data, the method further comprising:

determining that the respiratory rate data satisfies a threshold for at least a portion of the plurality of days, wherein identifying the one or more menstrual cycle phases in the inverted derivative of the time series is based at least in part on determining that the respiratory rate data satisfies the threshold.

10. The method of claim 1, further comprising:

determining each temperature value of the plurality of temperature values based at least in part on receiving the temperature data, wherein the temperature data comprises continuous daytime temperature data.

11. The method of claim 1, further comprising:

identifying additional menstrual cycle events based at least in part on determining the time series of the plurality of temperature values.

12. The method of claim 1, further comprising:

estimating a future menstrual cycle phase during which the user experiences a first day of a menstrual cycle based at least in part on at least the time series of the plurality of temperature values, the one or more menstrual cycle phases, or both.

13. The method of claim 1, further comprising:

measuring, continuously via one or more light-emitting components and one or more light-receiving components arranged on the surface of the wearable ring device, photoplethysmogram (PPG) data from an underside of the finger of the user.

14. The method of claim 1, further comprising:

causing the graphical user interface of the user device to display menstrual cycle symptom tags based at least in part on a correlation between prior user symptom tags and a timing of the one or more menstrual cycle phases.

15. The method of claim 1, further comprising:

estimating a length of a user's current menstrual cycle based at least in part on a morphology of the time series of the plurality of temperature values after a previous menstrual cycle.

16. The method of claim 1, further comprising:

identifying ovarian cycle events during the plurality of days based at least in part on the time series of the plurality of temperature values, wherein the one or more menstrual cycle phases comprises the ovarian cycle events.

17. The method of claim 1, further comprising:

identifying ovarian cycle events during the plurality of days based at least in part on heart rate data, respiratory rate data, or both, wherein the one or more menstrual cycle phases comprises the ovarian cycle events.

18. The method of claim 1, further comprising:

inputting the physiological data into a machine learning classifier, wherein identifying the one or more menstrual cycle phases is based at least in part on inputting the physiological data into the machine learning classifier.

19. The method of claim 1, further comprising:

receiving, via the user device and in response to identifying the one or more menstrual cycle phases, a confirmation of the one or more menstrual cycle phases.

20. The method of claim 1, further comprising:

receiving, via the user device, an indication of a menstrual cycle phase, one or more symptoms associated with the menstrual cycle phase, or both, wherein identifying the one or more menstrual cycle phases is based at least in part on receiving the indication of the menstrual cycle phase, the one or more symptoms associated with the menstrual cycle phase, or both.

21. The method of claim 1, further comprising:
causing the graphical user interface of the user device to display a message associated with the one or more menstrual cycle phases.

22. The method of claim 21, wherein the message comprises a time of day during which the one or more menstrual cycle phases occurred, a duration between a future menstrual cycle phase and a previous menstrual cycle phase, a time interval during which a future menstrual cycle phase is predicted to occur, a request to input symptoms associated with the one or more menstrual cycle phases, a medical condition associated with the one or more menstrual cycle phases, educational content associated with the one or more menstrual cycle phases, or a combination thereof.

23. The method of claim 1, wherein the wearable ring device collects the temperature data from the user based on arterial blood flow.

24. A system for identifying a menstrual cycle phase at a user device, comprising:
a wearable ring device configured to be worn on a finger of a user and acquire physiological data from the user, wherein the wearable ring device comprises:
a ring-shaped housing;
one or more temperature sensors arranged within the ring-shaped housing, wherein temperature data measured from the finger of the user captures a higher degree of temperature fluctuations as compared to core temperature measurements;
a plurality of sensors arranged on a surface of the ring-shaped housing; and
one or more processors disposed at least partially within the ring-shaped housing, wherein the one or more processors are electrically coupled with the one or more temperature sensors and the plurality of sensors;

a communication module electrically coupled with the one or more processors, wherein the communication module is configured to transmit the physiological data generated by the one or more processors, wherein the one or more processors are configured to:

measure, using the wearable ring device, the physiological data comprising at least temperature data;

determine, via the one or more processors, a time series of a plurality of temperature values taken over a plurality of days based at least in part on the temperature data, wherein the time series comprises a plurality of menstrual cycles for the user;

compute, via the one or more processors, a derivative of the time series of the plurality of temperature values;

invert, via the one or more processors, the derivative of the time series of the plurality of temperature values based at least in part on computing the derivative of the time series;

identify, via the one or more processors, one or more morphological features of the inverted derivative;

identify, via the one or more processors, one or more menstrual cycle phases in the time series based at least in part on identifying the one or more morphological features of the inverted derivative of the time series and the temperature data measured being indicative of the temperature fluctuations, wherein each menstrual cycle phase of the one or more menstrual cycle phases is associated with a morphological feature in the inverted derivative of the time series; and transmit, via the communication module, one or more signals to a user device to cause a graphical user interface of the user device to display the one or more menstrual cycle phases.

* * * * *